US007358091B2

(12) United States Patent
Phillips et al.

(10) Patent No.: US 7,358,091 B2
(45) Date of Patent: Apr. 15, 2008

(54) DEVICE AND METHODS FOR IDENTIFYING AND TREATING ASPIRIN NON-RESPONSIVE PATIENTS

(75) Inventors: David R. Phillips, San Mateo, CA (US); Patrick Andre, San Mateo, CA (US); Gillian Stephens, San Francisco, CA (US)

(73) Assignee: Portola Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 11/304,054

(22) Filed: Dec. 14, 2005

(65) Prior Publication Data

US 2006/0160165 A1 Jul. 20, 2006

Related U.S. Application Data

(60) Provisional application No. 60/636,744, filed on Dec. 14, 2004.

(51) Int. Cl.
*G01N 33/86* (2006.01)
(52) U.S. Cl. ........................................... 436/69
(58) Field of Classification Search ................ None
See application file for complete search history.

(56) References Cited

U.S. PATENT DOCUMENTS

2006/0211071 A1 9/2006 Andre

OTHER PUBLICATIONS

Andersen et al. Aspirin Non-Responsiveness as Measured by PFA-100 in Patients With Coronary Artery Disease; Thrombosis Research, vol. 108 (2003) pp. 37-42.*
Barstad et al. A Perfusion Chamber Developed to Investigate Thrombus Formation and Shear Profiles in Flowing Native Human Blood at the Apex of Well-Defined Stenosis; Arteriosclerosis, Thrombosis and Vascular Biology, vol. 14, No. 12 (1994) pp. 1984-1991.*
Cadroy et al. Early Potent Antithrombotic Effect With Combined Aspirin and a Loading Dose of Clopidogrel on Experimental Arterial Thrombogenesis in Humans; Circulation, vol. 101 (2000) pp. 2823-2828.*
Escolar et al. Inhibition of Platelet-Vessel Wall Interactions by Thromboxane Receptor Antagonism in a Human in Vitro System: Potentiation of Antiplatelet Effects in Aspirin; European Journal of Clinical Investigation, vol. 28 (1998) pp. 562-568.*
Bossavy et al. A Double-Blind Randomized Comparison of Combined Aspirin and Ticlopidine Therapy Versus Aspirin or Ticlopidine Alone on Experimental Arterial Thrombogenesis in Humans; Blood, vol. 92, No. 5 (1998) pp. 1518-1525.*
Osende et al. Antithrombotic Effects of S18886, A Novel Orally Active Thromboxane A2 Receptor Antagonist; Journal of Thrombosis and Haemostasis, vol. 2 (2004) pp. 492-498.*
Arrebola et al. In Vitro Effects of Clopidogrel on the Platelet-Subendothelium Interaction, Platelet Theomboxane and Endothelial Prostacyclin Production, and Nitric Oxide Synthesis; Journal of Cardiovascular Pharmacology; vol. 43, No. 1 (2004) pp. 74-82.*
Emery et al. Whole-Blood Platelet Aggregation Predicts in Vitro and in Vivo Primary Hemostatic Function in the Elderly; Ateriosclerosis, Thrombosis, and Vascular Biology, vol. 15 (1995) pp. 748-753.*
Andersen et al., "Aspirin Non-Responsiveness as Measured by PFA-100 in Patients with Coronary Artery Disease," *Thrombosis Research*, 2002; vol. 108, No. 1, pp. 37-42.
Andre et al., "Anticoagulants (Thrombin inhibitors) and Aspirin Synergize with P2Y12 Receptor Antagonism in Thrombosis", *Circulation*, 2003, vol. 108, No. 21, pp. 2697-2703.
Andre et al., "P2Y12 Regulates Platelet Adhesion/Activation, Thrombus Growth, and Thrombus Stability in Injured Arteries", *Journal of Clinical Investigation*, 2003, vol. 112, No. 3, pp. 398-406.
Antiplatelet Trialists' Collaboration, "Collaborative Meta-Analysis of Randomised Trials of Antiplatelet Therapy for Prevention of Death, Myocardial Infarction, and Stroke in High Risk Patients", *British Medical Journal*, 2002, vol. 324, No. 7329, pp. 71-86.
Antiplatelet Trialists' Collaboration , "Collaborative Overview of Randomised Trials of Antiplatelet Therapy—I: Prevention of Death, Myocardial Infarction, and Stroke by Prolonged Antiplatelet Therapy in Various Categories of Patients", *British Medical Journal*, 1994, vol. 308, No. 6921, pp. 81-106.
Barstad et al., "Reduced Effect of Aspirin on Thrombus Formation at High Shear and Disturbed Laminar Blood Flow", *Thrombosis Haemostasis*, 1996, vol. 75, No. 5, pp. 827-832.
Baumgartner et al., "Platelet Adhesion, Release and Aggregation in Flowing Blood: Effects of Surface Properties and Platelet Function", *Thrombosis Haemostais*, 1976, vol. 35, No. 1, pp. 124-138.
Catella-Lawson et al., "Cyclooxygenase Inhibitors and the Antiplatelet Effects of Aspirin", *The New England Journal of Medicine*, 2001, vol. 345, No. 25, pp. 1809-1817.
Chakroun et al., "In Vitro Aspirin Resistance Detected by PFA-100 Closure Time: Pivotal Role of Plasma von Willebrand factor", *British Journal of Haematology*, 2004, vol. 124, No. 1, pp. 80-85.
Eikelboom et al., "Aspirin-Resistant Thromboxane Biosynthesis and the Risk of Myocardial Infarction, Stroke, or Cardiovascular Death in Patients at High Risk for Cardiovascular Events." *Circulation*, 2002, vol. 105, No. 14, pp. 1650-1655.
Gum et al., "A Prospective, Blinded Determination of the Natural History of Aspirin Resistance Among Stable Patients with Cardiovascular Disease", *Journal of the American College of Cardiology*, 2003, vol. 41, No. 6, pp. 961-965.

(Continued)

*Primary Examiner*—Jon Weber
*Assistant Examiner*—Paul Martin
(74) *Attorney, Agent, or Firm*—Townsend and Townsend and Crew LLP

(57) ABSTRACT

The present invention relates to methods and compositions for identifying and treating subjects in need of antithrombotic therapies but who are not responsive to aspirin.

14 Claims, 25 Drawing Sheets

OTHER PUBLICATIONS

Gum et al., "Profile and Prevalence of Aspirin Resistance in Patients with Cardiovascular Disease", *The American Journal of Cardiology*, 2001, vol. 88, No. 3, pp. 230-235.

Helgason et al., "Development of Aspirin Resistence in Persons with Previous Ischemic Stroke", *Stroke*, 1994, vol. 25, No. 12, pp. 2331-2336.

International Stroke Trial Collaborative Group, "The International Stroke Trial (IST): a Randomised Trial of Aspirin, Subcutaneous Heparin, Both, or Neither Among 19435 Patients with Acute Ischaemic Stroke. International Stroke Trial Collaborative Group", *The Lancet*, 1997, vol. 349, No. 9065, pp. 1569-1581.

ISIS-2 Collaborative Group, "Randomised Trial of Intravenous Streptokinase, Oral Aspirin, Both, or Neither Among 17, 187 Cases of Suspected Acute Myocardial Infarction: ISIS-2. ISIS-2 (Second International Study of Infarct Survival) Collaborative Group", *The Lancet*, 1988, vol. 2, No. 8607, pp. 349-360.

Jenkins et al., "Systematic Review of Prevalence of Aspirin Induced Asthma and Its Implications for Clinical Practice", *British Medical Journal*, 2004, vol. 328, No. 7437, pp. 434.

Kawasaki et al., "Increased Platelet Sensitivity to Collagen in Individuals Resistant to Low-Dose Aspirin", *Stroke*, 2000, vol. 31, No. 3, pp. 591-595.

Macdonald et al., "Effect of Ibuprofen on Cardioprotective Effect of Aspirin", *The Lancet*, 2003, vol. 361, No. 9357, pp. 573-574.

Maclouf et al., "Eicosanoids and Iso-eicosanoids: Constitutive, Inducible and Transcellular Biosynthesis in Vascular Disease", *Thrombosis Haemostais*, 1998, vol. 79, No. 4, pp. 691-705.

Maugeri, et al., "Transcellular Metabolism of Arachidonic Acid: Increased Platelet Thromboxane Generation in the Presence of Activated Polymorphonuclear Eukocytes", *Blood*, 1992, vol. 80, No. 2, pp. 447-451.

Pulcinelli et al., "Inhibition of Platelet Aggregation by Aspirin Progressively Decreases in Long-Term Treated Patients", *Journal of American Cardiology*, 2004, vol. 43, No. 6, pp. 979-984.

Valles et al., "Erythrocyte Promotion of Platelet Reactivity Decreases the Effectiveness of Aspirin as an Antithrombotic Therapeutic Modality: the Effect of Low-Dose Aspirin is Less Than Optimal in Patients with Vascular Disease Due to Prothrombotic Effects of Erythrocytes on Platelet Reactivity", *Circulation*, 1998, vol. 97, No. 4, pp. 350-355.

Yin et al., "Antiaggregatory Activity of 8-Epi-Prostaglandin F2 Alpha and other F-Series Prostanoids and Their Binding to Thromboxane A2/prostaglandin H2 Receptors in Human Platelets", *The Journal of Pharmacology and Experimental Therapeutics*, 1994, vol. 270, No. 3 pp. 1192-1196.

Zimmermann et al., "Aspirin Resistance After Coronary Artery Bypass Grafting", *Journal of Thoracic and Cardiovascular Surgery*, 2001, vol. 121, No. 5, pp. 982-984.

\* cited by examiner

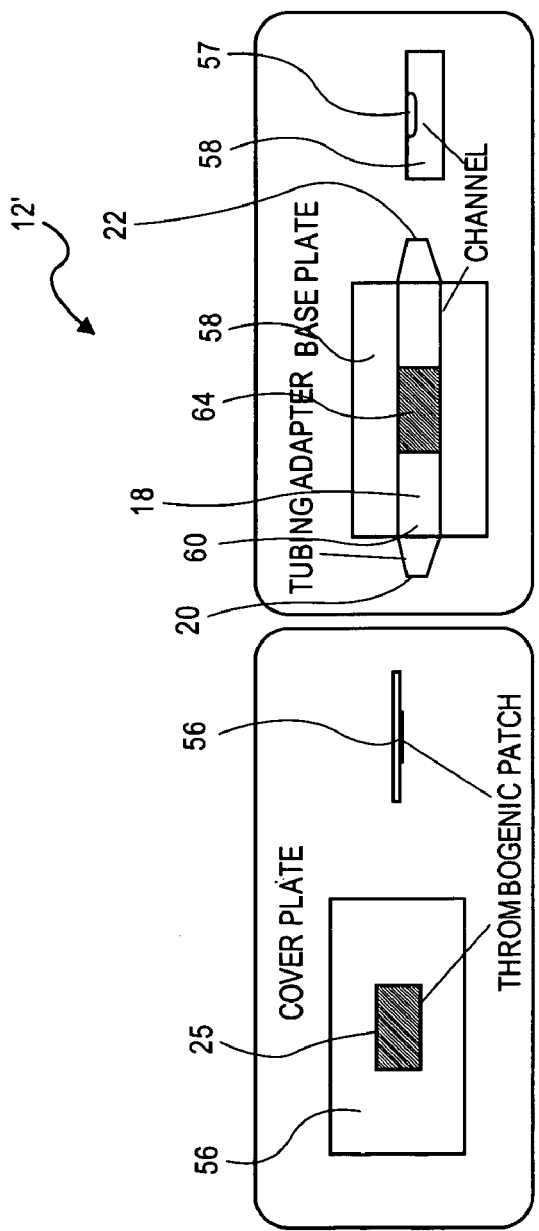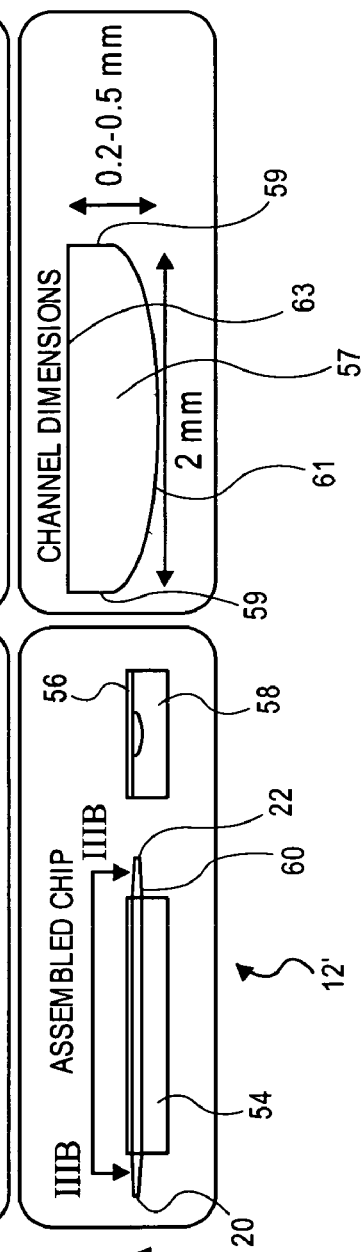

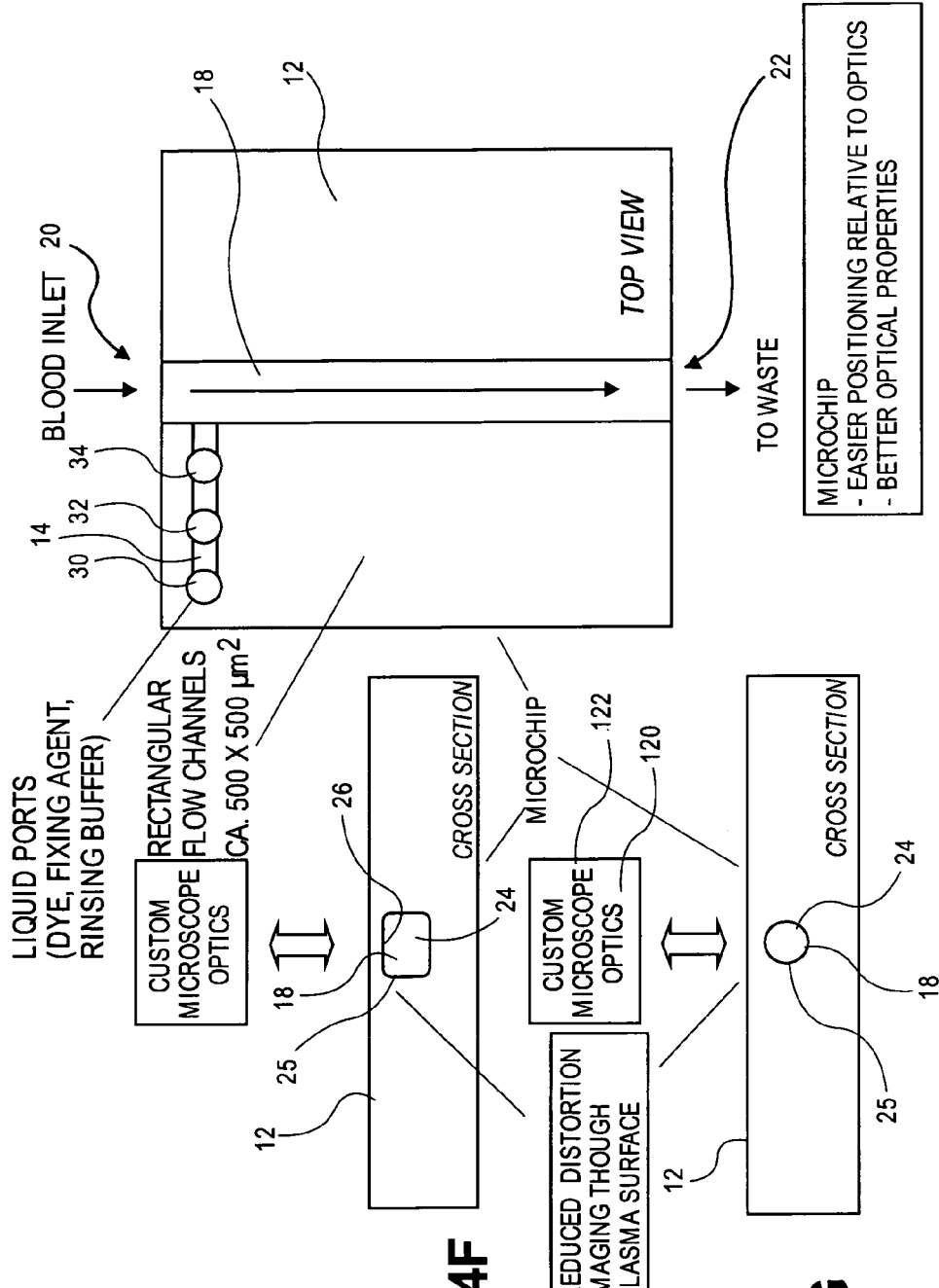

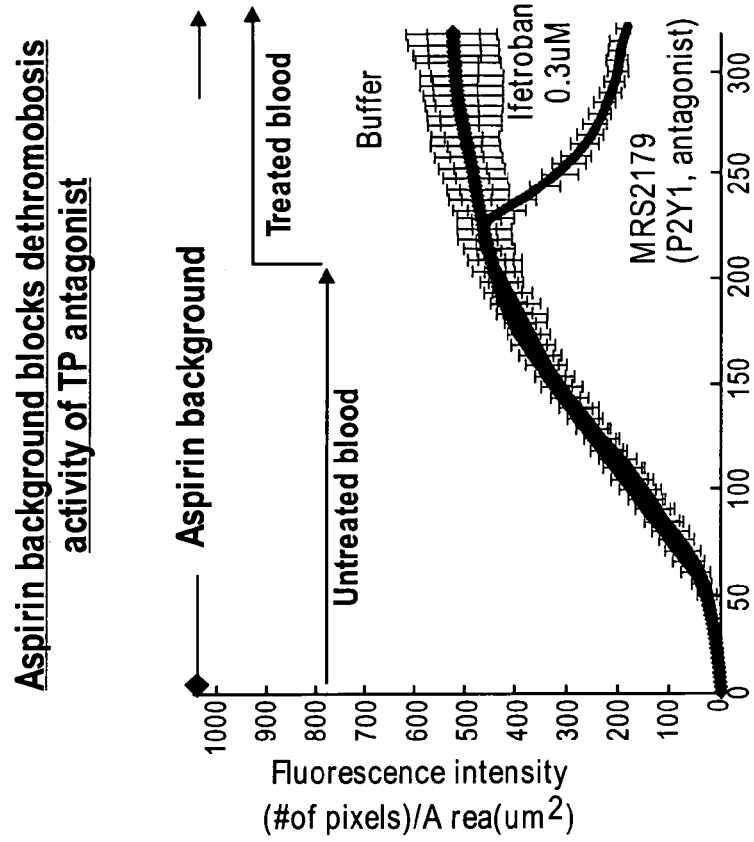
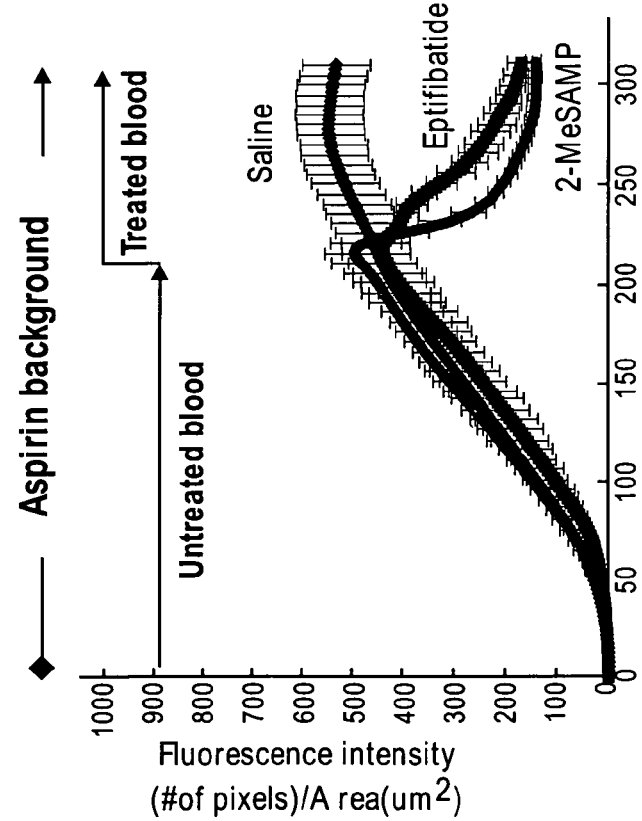
FIG. 12B
FIG. 12A

DEVICE AND METHODS FOR IDENTIFYING AND TREATING ASPIRIN NON-RESPONSIVE PATIENTS

CROSS-REFERENCES TO RELATED APPLICATIONS

This application claims the benefit of U.S. patent application Ser. No. 60/636,744, filed Dec. 14, 2004, which is herein incorporated by reference in its entirety.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

1. Aspirin Effects and Aspirin Resistance

Aspirin is known to reduce post-acute myocardial infarction (AMI) cardiovascular events by 25-30%. Recent findings indicate that the incidence of aspirin non-responders is between 5-40% of the treated population. It has been proposed that this sub-population of patients does not benefit from aspirin treatment and has an increased risk for future cardiovascular events. Although bedside devices exist for monitoring platelet function, these devices were not designed to specifically examine aspirin non-responsiveness. Therefore, the real prevalence of aspirin non-responders remains unknown. Moreover, existing bedside platelet monitoring devices are affected by platelet P2 receptor $P2Y_{12}$ antagonism. $P2Y_{12}$ antagonism induced by PLAVIX (clopidogrel bisulfate) which is commonly prescribed for patients with acute coronary syndromes (ACS). Since this patient population is at high risk for thrombotic events, and has been found to have a high incidence of aspirin non-responsiveness, and since PLAVIX (clopidogrel bisulfate) requires aspirin co-therapy to be maximally effective, effective management of this patient population requires that new platelet monitoring devices and methods be employed.

One method for detecting aspirin resistance in the background of PLAVIX (clopidogrel bisulfate) use comprises the step of evaluating simultaneously in real time the effect of aspirin on thrombus formation triggered by a collagen-coated capillary and by arachidonic acid-induced whole blood thrombus formation under arterial shear rates.

The antithrombotic properties of aspirin were reported more than 50 years ago and are mostly attributed to the inhibition of prostaglandin synthesis. Aspirin treatment is known to exhibit both anti-thrombotic and anti-inflammatory activities, thought to be mediated by irreversible acetylation of Ser530 of cycloxygenase type 1 (Cox-1) and Ser516 of cycloxygenase type 2 (Cox-2), respectively. Cox-1 is constitutively expressed whereas Cox-2 is inducible. This is of particular importance when evaluating the anti- and potential pro-thrombotic activities of aspirin. As platelets are anucleate cells, aspirin inhibition of the synthesis of the pro-aggregatory and vasoconstrictor metabolite thromboxane A2 (TxA2) lasts for the life of the cell even though aspirin's half life is only 20 minutes. By comparison, aspirin inhibition of Cox-2, and the subsequent prevention of prostacyclin (PGI2) by endothelial cells is rapidly overcome by newly synthesized Cox-2. Resynthesis of Cox-2 is judged to be beneficial as PGI2 is antiaggregatory and vasodilatory. Benefits of aspirin therapy in cardio/cerebrovascular diseases are well documented. For example, aspirin is known to reduce the incidence of AMI in the acute phase of unstable angina by up to 25% (*Lancet*, 2(8607): 349-60 (1988); *Bmj*, 308(6921):81-106 (1994)), and to reduce mortality and recurrent stroke in patients with acute ischemic stroke (*Lancet*, 349(9065):1569-81 (1997)). A meta-analysis recently suggested that the use of aspirin in patients population with diabetes and peripheral arterial disease be expanded (*Bmj* 324(7329):71-86 (2002)).

However, in the past 15 years there have been several studies reporting the existence of a sub-population of patients resistant to the antithrombotic activity of aspirin. The prevalence of aspirin resistance is reported to range between 5 and 40%. The broad range is attributed to the absence of a reliable assay that will specifically assess the antithrombotic properties of aspirin.

Several hypotheses have been proposed for aspirin resistance, some of which concern aspirin, others not: Cox-2 expression in platelets, Cox-2 activation in inflammatory and vascular cells, and/or production of eicosanoids, increased reaction to collagen or adenosine diphosphate (ADP), presence of erythrocytes, interaction between aspirin and non-steroidal anti-inflammatory drugs (NSAIDs), variant isoforms of Cox-1, increased platelet turnover, poor compliance, increased amount of plasma von Willebrand factor (vWF), or genetic polymorphisms (of glycoprotein IIb-IIIa (GP IIb-IIIa), GP Ia-IIa, and eventually GP Ibα). Several studies have shown that aspirin resistance may be inducible. For example, one study showed that about 30% of people become resistant while under chronic aspirin therapy (Helgason, C. M. et al., *Stroke*, 25(12):2331-6 (1994)) and another showed that an increase in percentage of aspirin-resistant patients occurs following surgical procedures (i.e. post coronary artery bypass grafting (CABG), Zimmermann, N. et al., *J Thorac Cardiovasc Surg*, 121(5):982-4 (2001)). Others have reported a progressive reduction in platelet sensitivity to aspirin as measured by platelet aggregation in long-term treated patients (Pulcinelli, F. M. et al., *J Am Coll Cardiol*, 43(6):979-84 (2004)). Moreover, the lack of reliable tools that specifically measure aspirin effects may directly contribute to the extent of the aspirin resistance phenomenon. Indeed, aspirin resistance may be also dose-dependent, and it is plausible that part of the aspirin resistant population could benefit from a personalized therapy. The development of an assay that will allow quantitative assessment of these issues is therefore necessary.

The clinical consequences of aspirin resistance are of major importance as it is now commonly accepted that it correlates with future cardiovascular events (Gum, P. A. et al., *J Am Coll Cardiol*, 41(6):961-5 (2003); Eikelboom, J. W. et al., *Circulation*, 105(14):1650-5 (2002)). An example of aspirin resistance that may correlate with thrombotic events is the interaction of aspirin with NSAIDs. It has been reported that the aspirin-dependent inhibition of platelet aggregation and serum TxB2 formation (stable metabolite of TxA2) was compromised when ibuprofen was administered prior to aspirin (Catella-Lawson, F. et al., N Engl J Med, 345(25): 1809-17 (2001)). The binding of ibuprofen is proposed to block the S530 site of Cox-1 before its irreversible acetylation by aspirin. This important finding appears to correlate with clinical events as a recent study has highlighted an increased cardiovascular mortality in patients combining ibuprofen plus aspirin vs aspirin alone (MacDonald, T. M. et al., *Lancet*, 361 (9357): 573-4 (2003)). The importance of aspirin resistance is further emphasized by the state of the art combination aspirin/P2Y$_{12}$ inhibition (PLAVIX (clopidogrel bisulfate)), demonstrated to confer higher antithrombotic efficacy than single therapies alone.

A clear, unequivocal definition of aspirin resistance becomes crucial as it could ultimately lead to a personalized antithrombotic strategy. The need for individualized screening is reinforced by the fact aspirin causes gastro-intestinal (GI) and bleeding complications. The GI toxicity of aspirin appears to be dose-dependent, starting with doses as low as 10 mg/day. Since other platelet-inhibiting and anticoagulant agents potentiate the gastro-intestinal lesions and bleeding risk associated with low-dose aspirin, one can therefore question the use of aspirin in aspirin-resistant patients. Moreover, aspirin's side effects are not limited to GI and bleeding complications. Aspirin is thought to induce asthma in as much as 20% of the patients (Jenkins, C. J. et al., *Bmj*, 328(7437):434 (2004)). This situation is rendered even more paradoxical as a high percentage of patients with aspirin-induced asthma also take NSAIDs (notably ibuprofen).

2. Laboratory Methods to Detect Aspirin Resistance:

Several laboratory tests of platelet function have been designed and are available to "diagnose" aspirin-resistance using whole blood. Most certainly, the 2 main tools utilized are the Ultegra Rapid Platelet Function Assay (RPFA-ASA), and the PFA-100 device.

The RPFA-ASA cartridge has been specifically designed to address the level of inhibition of platelet aggregation achieved by aspirin treatment. As mentioned by the manufacturer, it is a qualitative measure of the effects of aspirin. In that assay, fibrinogen-coated beads agglutinate platelets through binding to GP IIb-IIIa receptors following stimulation by metallic cations and propyl gallate. The change in optical signal triggered by the agglutination (light transmittance increases as activated platelets bind and agglutinate the beads in the whole blood suspension) is measured. A recent study has detected a high incidence (23%) of aspirin non-responsiveness using this device, and determined a history of coronary artery disease to be associated with twice the odds of being an aspirin non-responder (Wang, J. C. et al., *Am J Cardiol*, 92(12): 1492-4 (2003)). Aspirin resistance cannot be evaluated by the RPFA assay, however, in patients who were prescribed either GP IIb-IIIa inhibitors, dipyridamole, PLAVIX (clopidogrel bisulfate) (or TICLID (ticlopidine HCI), or NSAIDS (ibuprofen, naproxen, diclofenac, indomethacin, piroxicam) since those compounds interfere with the assay.

In the PFA-100 device, the platelet hemostatic capacity (PHC) of a citrated blood sample is determined by the time required for a platelet plug to occlude a 150 μM aperture cut into a collagen-epinephrine coated membrane (used for the detection of aspirin). In the PFA-100 system, samples of citrated blood are aspirated through the aperture at shear rates of ~4,000-5,000/sec. Under these high conditions of shear, vWF interactions with both GP Ibα and GP IIb-IIIa trigger the thrombotic process. In the context of clinical events, plasma levels of vWF are expected to increase following platelet-rich thrombi formation and endothelial cell injury. Interestingly, Chakroun et al. reported that the aspirin-resistant population measured by PFA-100 also demonstrated an increased plasma vWF ristocetin cofactor activity (Chakroun, T. et al., *Br J Haematol*, 124(1):80-5 (2004)). Furthermore, a poor inhibition of thrombotic events has been reported for shear rates around 10,000/sec with aspirin (Barstad, R. M. et al., *Thromb Haemost*, 75(5):827-32 (1996)), and PFA-100 detects desmopressin (DDAVP) therapy which increases plasma levels of vWF (Fressinaud, E. et al., *Br J Haematol*, 106(3):777-83 (1999)). One can therefore argue that the high incidence of aspirin resistance found post-AMI with the PFA-100 device (Gum, P. A. et al., *Am J Cardiol*, 88(3):230-5 (2001)) reflects an increase in platelet sensitivity towards high shear induced collagen-vWF/GP Ibα-/GP IIb-IIIa-interactions (Chakroun, T. et al., *Br J Haematol*, 124(1):80-5 (2004)) rather than true aspirin resistance. In addition, several investigators have found that most of the aspirin-resistant population identified by PFA-100 appeared to be aspirin sensitive as shown by inhibition of platelet aggregation induced by arachidonic acid (AA) (Gum, P. A. et al., *J Am Coll Cardiol*, 41(6):961-5 (2003); Chakroun, T. et al., *Br J Haematol*, 124(1):80-5 (2004)), as well as extremely low TxB$_2$ levels (Andersen, K. *Thromb Res*, 108(1):37-42 (2002)). Moreover, investigators have reported a good prognosis for long term clinical events in the aspirin-resistant population revealed by AA-induced platelet aggregation, but this was not the case for the PFA-100 device. The data described herein also show that the PFA-100 device does not specifically reveal aspirin effects.

Other models have been utilized for examining aspirin effects, such as platelet aggregation and bleeding time. For example, arachidonic acid-induced platelet aggregation in platelet rich plasma is classically considered the gold standard for evaluation of aspirin effects on platelets. Nevertheless, determining aspirin resistance should be investigated using whole blood for several reasons. First, erythrocytes may contribute to aspirin-resistance. Valles et al. (Valles, J. et al., *Blood*, 78(1):154-62 (1991)) have demonstrated that the presence of erythrocytes directly affects platelet reactivity by increasing TxB$_2$ synthesis, release of serotonin (5-HT), β-thromboglobulin (β-TG) and ADP. This has a major impact on the evaluation of aspirin resistance, as the same authors found that aspirin treatment (200-300 mg daily) failed to block platelet reactivity in presence of erythrocytes in two thirds of a group of patients with ischemic heart disease and ischemic stroke, despite full inhibition of TxA2 synthesis (Valles, J. et al., *Circulation*, 97(4):350-5 (1998)).

Second, nucleated cells (leukocytes) may contribute to aspirin-resistance. It is commonly accepted that because platelets are anucleated cells, their potential for producing TxA$_2$ is irreversibly suppressed during their lifetime after aspirin treatment. However, a potential source of aspirin-insensitive TxA$_2$ and 8-epi-prostaglandin-F 2α (8-epi PGF$_{2\alpha}$) (2 known platelet agonists) exists as the de novo synthesis of Cox-2 and full recovery of Cox activity occurs 2 to 4 hours after aspirin treatment via stimulated nucleated cells (Maclouf, J. G. et al., *Thromb Haemost*, 79(4):691-705 (1998)). Platelet microparticles can also indirectly participate in generation of Cox-2-dependent TxA$_2$ formation via delivery of AA by sPLA$_2$. Similarly, it has been reported that AA derived from neutrophils can increase TxA$_2$ formation in platelets (Maugeri, N. et al., *Blood*, 80(2):447-51 (1992)).

Third, plasma proteins and lipids may contribute to aspirin-resistance. The presence of F2-isoprostanes in plasma are increased in patients with unstable angina, diabetes mellitus, hypercholesterolemia and cigarette smokers. These sub-populations present some of the highest percentage of aspirin-resistant patients. One candidate for mediating aspirin resistance is the 8-epi-PGF$_{2\alpha}$ or isoprostane 8-epi prostaglandin F$_{2\alpha}$ (8-iso-PGF$_{2\alpha}$). It is produced from AA by nonenzymatic lipid peroxidation catalyzed by oxygen free radicals, and is aspirin-insensitive (Wang, Z. et al., *J Phar-* macol Exp Ther, 275(1):94-100 (1995)). Consequently, 8-epi-PGF$_{2\alpha}$ generation can occur in all cellular players of atherosclerosis. It is a potent vasoconstrictor and has been reported to activate platelets at high concentrations and cause dose-dependent irreversible platelet aggregation in the presence of subluminal concentrations of collagen, ADP or arachidonic acid. In addition, 8-epi-PGF$_{2\alpha}$ could potentiate the expression of GP IIb-IIIa and enhance platelet adhesion on fibrinogen. Although a direct interaction of 8-epi-PGF$_{2\alpha}$ with the TPα receptor has been shown, the biological significance of 8-epi-PGF$_{2\alpha}$ in thrombosis remains controversial as low concentrations (such as those found in vivo) may inhibit collagen-induced platelet aggregation but amplify low dose ADP-induced platelet aggregation (Yin, K. et al., *J Pharmacol Exp Ther*, 270(3):1192-6 (1994)).

Whole blood platelet aggregation and whole blood aggregation utilizing a screen filtration pressure method have been shown to detect the effects of aspirin. However, these are labor intensive techniques and the evaluation of the aggregation process is performed under low shear rate conditions (like those encountered in veins) which do not reflect the thrombotic process occurring in moderately stenosed arteries.

Template bleeding times have been demonstrated to be accurate in determining platelet function prior to and following ASA administration. This technique is sensitive enough to diagnose platelet dysfunction (notably von Willebrand Disease), but bleeding time is highly variable, and sensitive to all anti-platelet agents, anti-coagulants, and other factors such as alcohol and green tea.

Altogether, the different techniques are either time-consuming, or of poor prognostic for true aspirin resistance. This demonstrates the need for a new device and methods that will specifically evaluate aspirin effects.

BRIEF SUMMARY OF THE INVENTION

In one embodiment, the present invention provides a method of evaluating aspirin responsiveness in a subject, comprising:

(a) perfusing a blood sample from a subject through a channel in a perfusion device, wherein the channel has a coating which produces a blood deposit when exposed to blood and wherein the perfusion device comprises a pump which draws the blood through the channel at a selected shear rate, producing a blood deposit; and (b) determining a status of aspirin responsiveness by measuring the level of blood deposited in the chamber and comparing the measured level of deposited blood with a control level of deposited blood, wherein said control level is selected from the group consisting of (1) a level measured using a sample of blood from said subject which has been treated with aspirin; (2) a level measured using a sample of blood from said subject which has been contacted with a thromboxane A2 receptor antagonist; and (3) a level previously determined to correspond to a status of aspirin responsiveness.

In another embodiment, the present invention provides a method of qualifying a subject for treatment with a thromboxane A2 receptor antagonist, comprising:

(a) perfusing a blood sample from said subject through a channel in a perfusion device, wherein the channel has a coating which produces a blood deposit when exposed to blood and the perfusion device comprises a pump coupled to the outlet end of the housing to draw the blood through the channel at a desired shear rate, producing a blood deposit, and wherein said blood sample is treated with an amount of a platelet ADP receptor antagonist sufficient to inhibit thrombosis at least approximately 20% relative to an untreated sample; and (b) wherein said blood sample is treated with an amount of aspirin sufficient to cause at least an approximately 50% inhibition of thrombosis in a blood sample relative to an untreated sample; and (c) wherein a subject is qualified for treatment with a thromboxane A2 receptor antagonist if less than approximately 50% inhibition of thrombosis is observed in said blood sample relative to an untreated sample.

BRIEF DESCRIPTION OF THE DRAWINGS

The accompanying drawings, which are incorporated herein and constitute part of this specification, illustrate an embodiment of the invention, and, together with the general description given above and the detailed description given below, serve to explain the features of the invention.

FIG. 1 shows that the effects of PLAVIX (clopidogrel bisulfate) will prevent the use of the RPFA-ASA cartridge in the ACS patient population. Whole blood was drawn into 3.2% Sodium citrate vacuum tubes and analyzed using the Ultegra RPFA-ASA assay. Sample results are based on the extent of platelet aggregation, reported in Aspirin Reaction Units (ARU). ARU.gtoreq.250 is consistent with no platelet dysfunction, ARU<550 is consistent with platelet dysfunction due to aspirin.

FIG. 4A-4D are views of another example of the member.

FIG. 4E-4G are a top and plan views of another example of the member.

FIG. 12A shows aspirin background and FIG. 12B shows how the aspirin background blocks dethrombosis activity of TP antagonist.

DETAILED DESCRIPTION OF THE INVENTION

I. Definitions

Before describing the present invention in detail, it is to be understood that this invention is not limited to particular compositions or methods, which can, of course, vary. It is also to be understood that the terminology used herein is for the purpose of describing particular embodiments only, and is not intended to be limiting. Further, unless defined otherwise, all technical and scientific terms used herein have the same meaning as commonly understood by one of ordinary skill in the art to which this invention pertains. In describing and claiming the present invention, the following terminology and grammatical variants will be used in accordance with the definitions set forth below.

The term "perfusing" means moving a fluid through, over or across something such a particular media.

Perfusion Assays

In one embodiment, the present invention provides a method of evaluating aspirin responsiveness in a subject, comprising perfusing a blood sample from a subject through a channel in a perfusion device. Perfusion devices have existed for over 30 years and were designed in order to characterize the thrombotic process under shear conditions. Several different types of perfusion chambers are described in the literature and can be classified according to their geometry (circular, annular, flat chambers) or the surfaces (blood vessels, isolated proteins) exposed to the blood flow. Examples of perfusion devices are disclosed in U.S. patent application Ser. No. 60/635,659, filed Dec. 14, 2004, and U.S. patent application entitled "A Device for Aggregating, Imaging and Analyzing Thrombi and a Method of Use", filed on Dec. 14, 2005 having Morgan, Lewis & Bockius LLP which are herein incorporated by reference in their entirety.

Figure 2A:
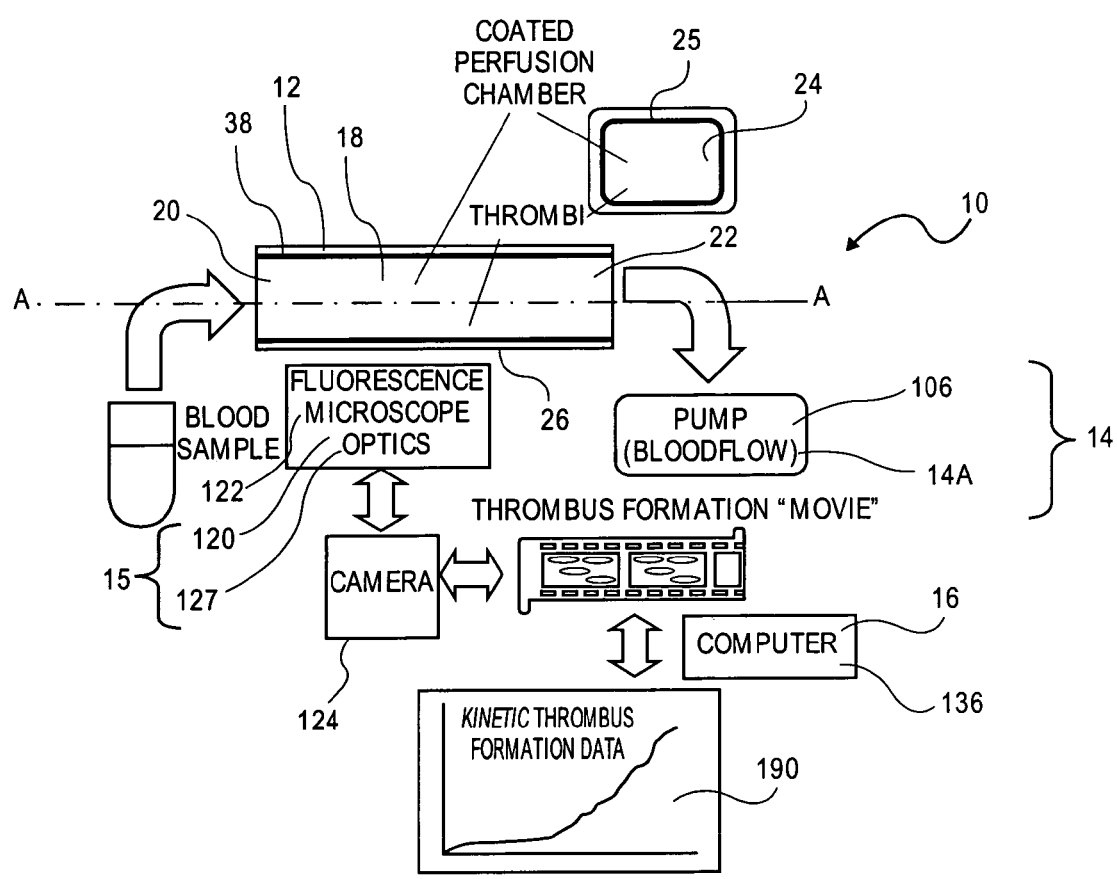
FIG. 2A is a schematic view of a perfusion device used in the aggregation of platelets to image and analyze thrombus formations.
Figure 2B:
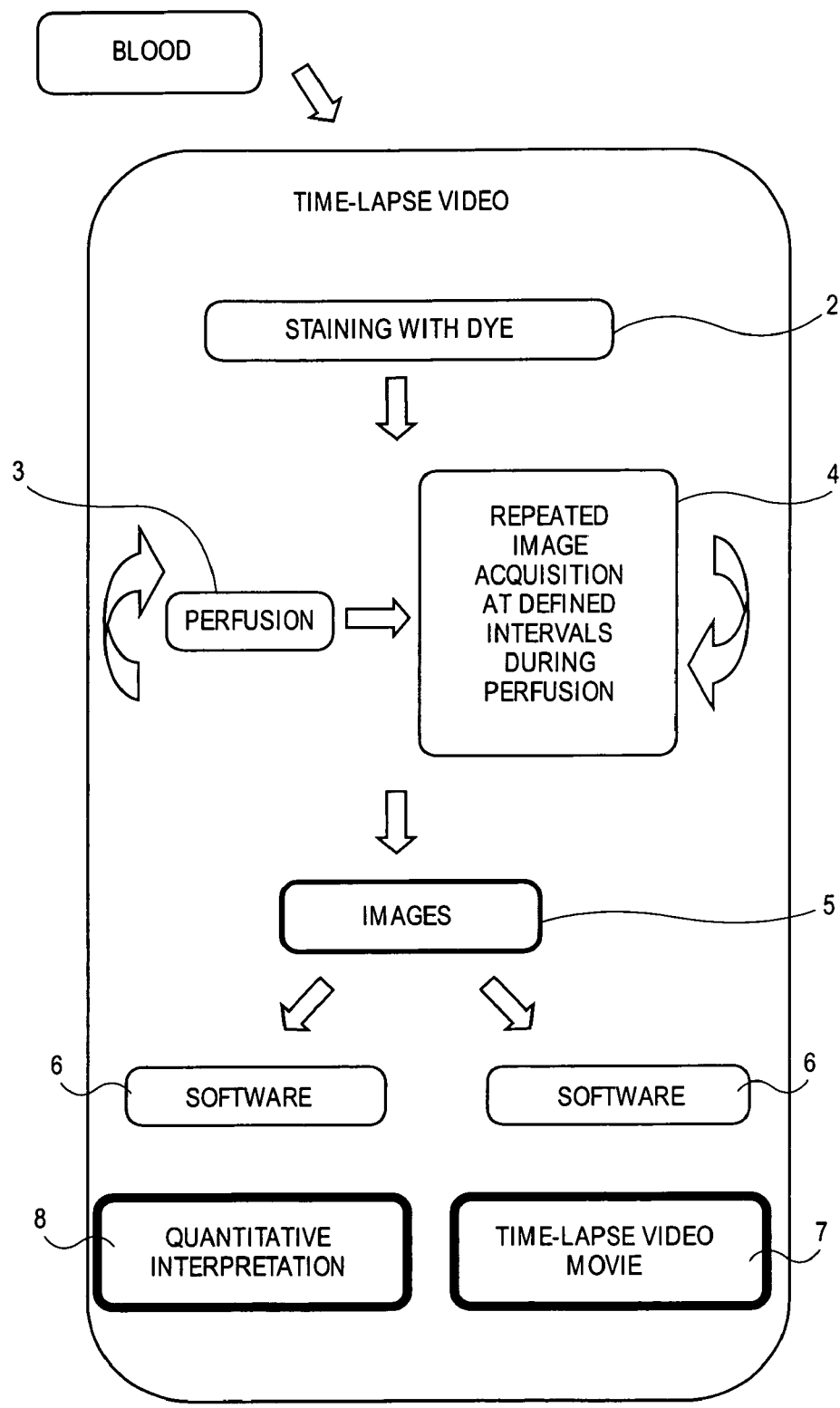
FIG. 2B is a flowchart of an embodiment of operation of the perfusion device of FIG. 2A.

One example of a perfusion device is shown in FIG. 2A. FIG. 2A is a schematic diagram of a perfusion device 10, in the form of a kinetic aggregometer instrument for capturing the kinetics or a moving or time-lapse image of thrombus formation, coagulation, leukocyte or tumor cell recruitment in a blood sample. To image the thrombus formation, the perfusion device 10 may use microscopy and/or micro-videography techniques, and in other embodiments light microscopy techniques. Shown in FIG. 2B is a flowchart of the operation of the perfusion device 10. Referring to both FIGS. 2A & 2B, the perfusion device 10 includes a member 12, a fluid handling assembly 14, an imaging assembly 15, and a data analyzer 16. According to box steps 2 and 3 in FIG. 2B, a sample of blood can be pre-treated with an imaging agent or fluorescent label and moved or perfused through member 12 by the fluid handling assembly 14 for a period of time so as to initiate thrombus formation within the member 12. Alternatively, the imaging agent can be added to the sample during the perfusion process. The imaging assembly 15 in box step 5 repeatedly images the developing thrombus formation within the member 12 during the perfusion using a camera 124 capable of motion capture. The imaging assembly 15 can use light microscopy and/or micro-videography techniques with fluorescence illumination. The image can be captured as time-lapsed digital image data and integrated over time to provide a movie or motion picture display of the evolving thrombus formation as is indicated by step boxes 6 and 7. In addition, the digital image data can be processed and correlated by analyzer 16 to quantify a temporal evolution of volume of thrombus formation or other quantifiable characteristics of thrombi formation, as is indicated by step boxes 6 and 8. This information can be useful in determining the real time efficacy of a given anti-thrombotic therapy using, for example: aspirin, $P2Y_{12}$ receptor targeted compounds and GPIIb/IIIa antagonists, Integrilin as well as other platelet-thrombus modulators, and can serve as feedback information to modifying the dosage of the therapy. The imaging assembly 15 can additionally include a non-imaging photodetector 127 that generates a signal in response to the fluorescence intensity of the thrombus formation. The signal can be used by the data analyzer 16 to correlate and quantify, in an alternate manner, the temporal evolution of the thrombus volume, in addition to other quantifiable characteristics of thrombus formation.

Figure 2C:
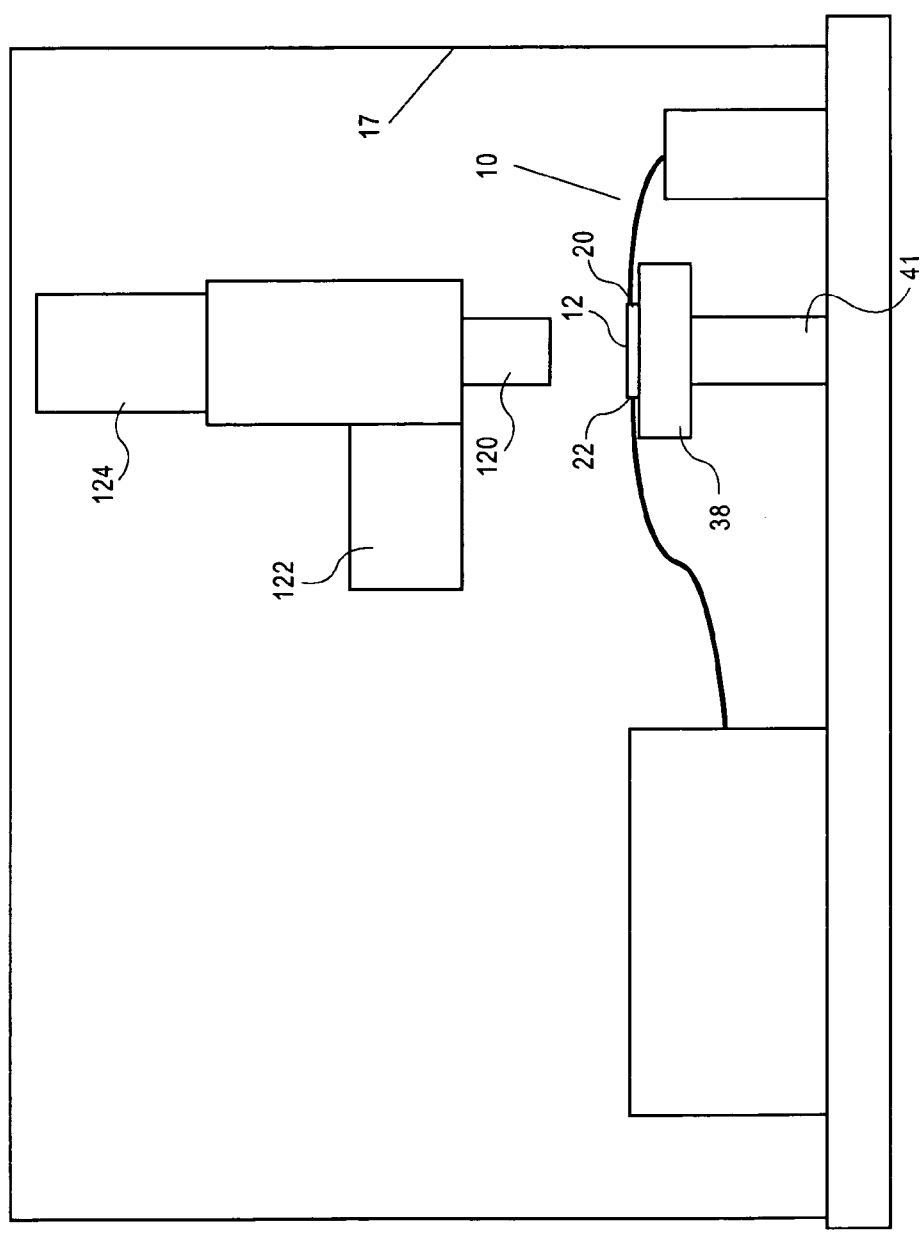
FIG. 2C is an alternative depiction of a perfusion device of FIG. 2A.
Figure 2D:
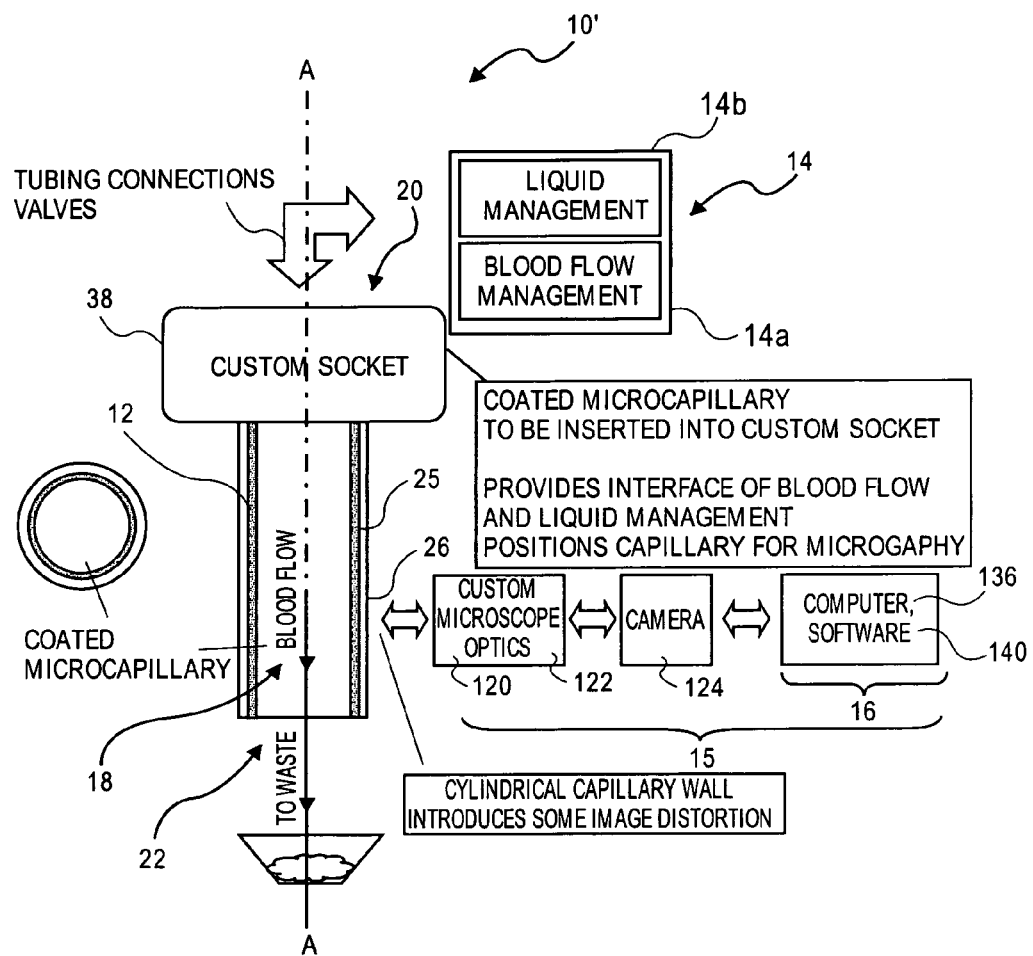
FIG. 2D is a schematic of another perfusion device used in the aggregation of platelets to produce thrombus formations and also used in the imaging and analysis of the formations.
Figure 2E:
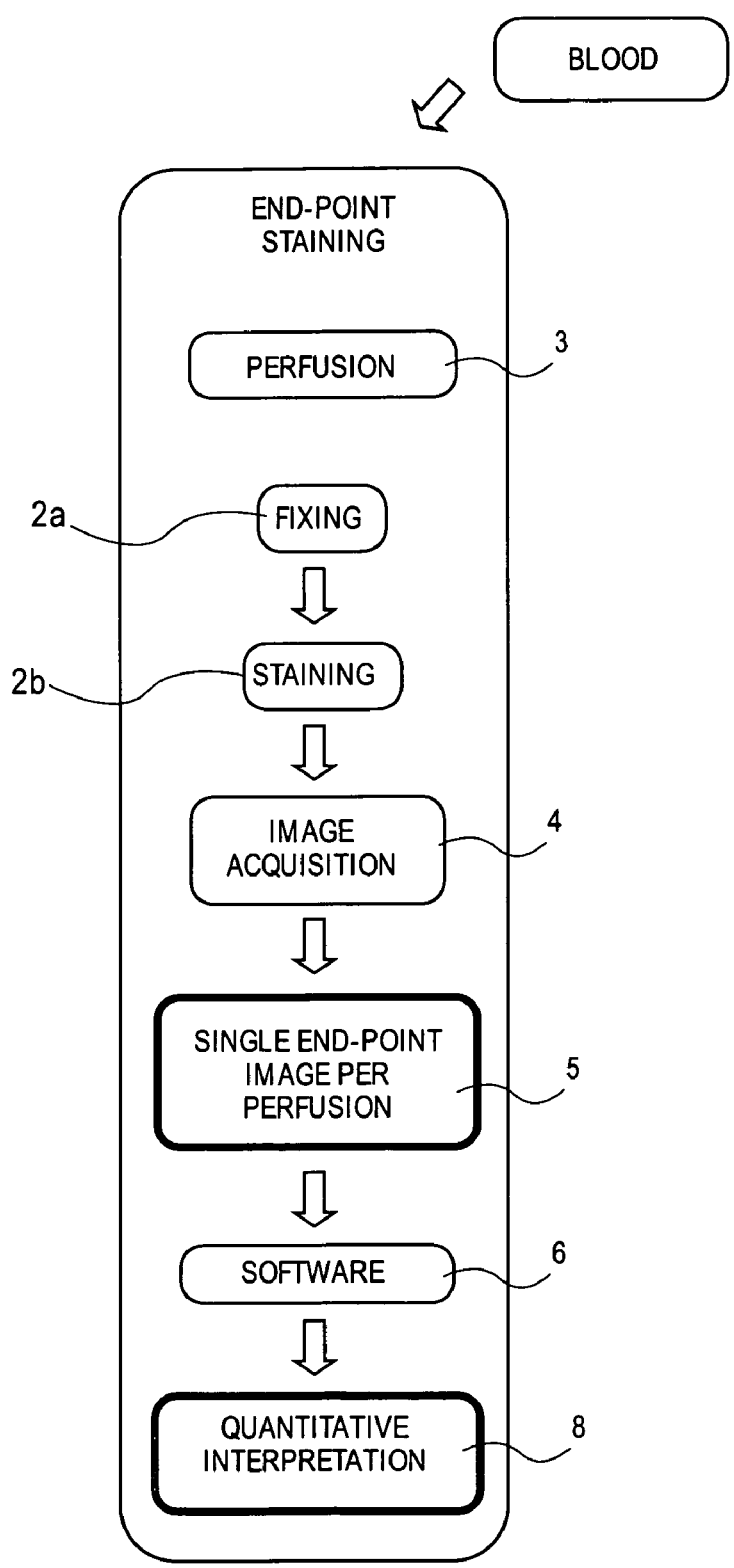
FIG. 2E is a flowchart of the operation of the perfusion device of FIG. 2D.

Alternatively as shown in FIG. 2D the perfusion device 10' can be configured for fixed imaging or "end-point measurement" of thrombi. Specifically, perfusion device 10' is configured for imaging the thrombus formation at a fixed point in time, preferably at the conclusion of the thrombus formation process using light microscopy techniques. Shown in FIG. 2E is a flow chart of the operation the perfusion device 10' in FIG. 2D.

Perfusion device 10', like perfusion device 10 of FIG. 2A, can also generally include a member 12, a fluid handling assembly 14, an imaging assembly 15, and an analyzer 16. Referring to both FIGS. 2D and 2E, the fluid handling assembly 14 of perfusion device 10' perfuses or moves a sample of blood through member 12 for a period of time so as to initiate thrombus formation within the member 12. The sample of blood can be subsequently treated with image enhancing agents that fix and stain the thrombus formation within the member 12, as is shown by step boxes 2a and 2b. The image enhancing agents can be delivered by the fluid handling assembly 14. The imaging assembly 15 can image the thrombus formation formed within the member 12 using microscopy techniques known to one of ordinary skill in the art, as indicated in step boxes 4 and 5. The imaging assembly 15 of perfusion device 10' may use light microscopy with Köhler illumination. The imaging assembly 15 can additionally capture the image as digital image data using a camera 124. The digital image data can be further processed by analyzer 16 in order to determine the volume of thrombus formation and other quantifiable characteristics of thrombus formation, such as for example, height, area and perimeter of the thrombus formation.

The member 12 can be configured for capturing the thrombus formation to be imaged and may be used in systems using either kinetic imaging or fixed end-point imaging of the thrombus formation. The member 12, shown for example in FIG. 2A, can be configured such that the surfaces of the member 12 define a flow channel 18 having an inlet end 20 and an outlet end 22. At least one of the surfaces 26 defining the channel 18 is transparent so as to make the blood sample in the flow channel visible for purposes of observing the thrombus formation under known microscopy or micro-videography techniques.

Figure 3A:
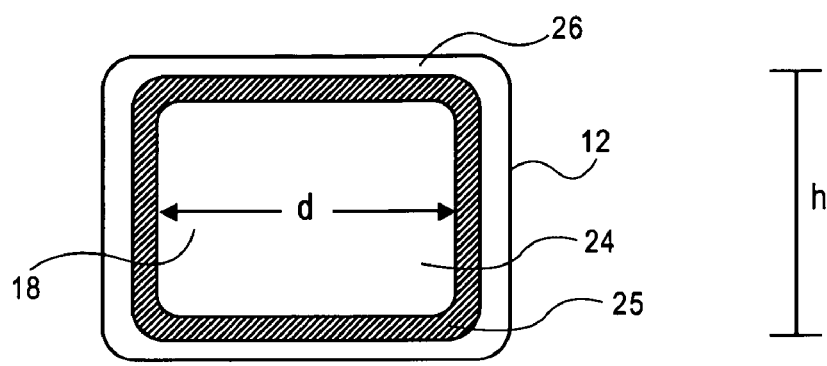
FIG. 3A-C are cross-sectional views of various examples of a member used in the perfusion device of FIG. 2 to aggregate platelets and produce thrombus formations.
Figure 3B:
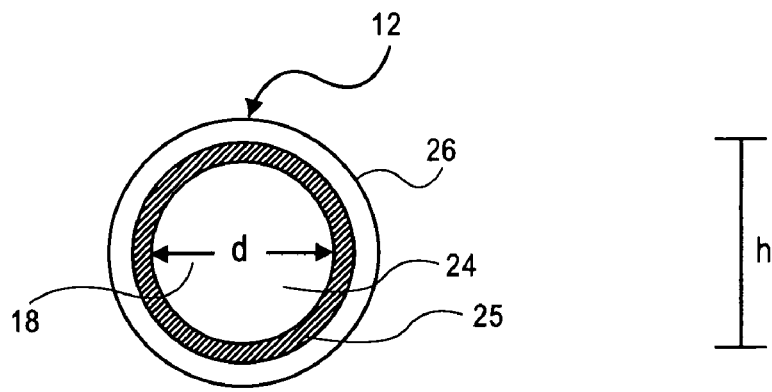
Figure 3C:
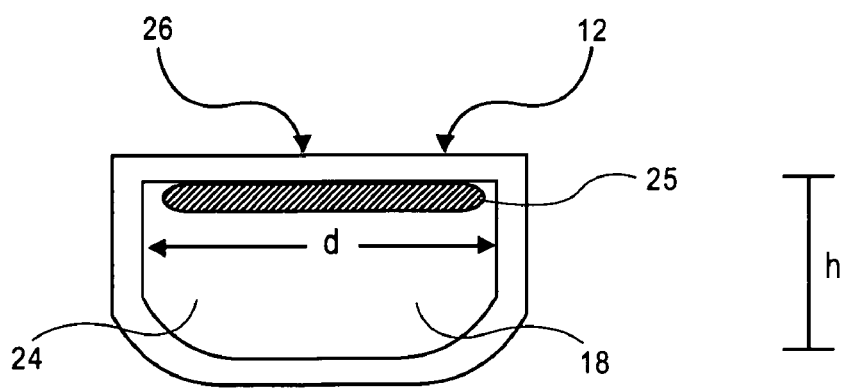

The transparent surface 26 is typically made of a non-thrombogenic material, for example, silica materials such as quartz, fused silica, boro silicate glass, plexi-glass or any other glass or plastic surface appropriate for thrombus formation when coated and capable of imaging formation readouts. Member 12 can be made completely of transparent non-thrombogenic material, such as where member 12 is, for example, a micro-capillary tube having a substantially circular cross-section 24. For example, member 12 may be a micro-capillary tube with a central through bore defining flow channel 18. As seen in FIG. 2A, the flow channel 18 defines a longitudinal axis A-A along which the sample of blood can flow. Typically, flow channel further defines a holding volume of about 20 µl or less, although channel 18 can be configured to hold larger volumes to suit a given assay. Referring to FIGS. 3A-3C, the flow channel 18 further defines a cross-sectional area 24 perpendicular to the longitudinal axis A-A which can be of any geometry. The cross-sectional area 24 may be substantially rectangular in shape as seen in FIG. 3A, or alternatively the cross-sectional area 24 can be substantially circular in shape, as is shown in FIG. 3B or substantially semi-circular in shape, as shown in FIG. 3C, although other configurations are possible.

The flow channels 18 of FIGS. 3A-3C define a channel width "d" and height "h". Preferably, height h is about 200 microns and width d of about 2 mm, more preferably less than about 1.5 mm, even more preferably less than about 1 mm, even more preferably less than about 500 microns and yet even more preferably less than about 400 microns. The channel width d can be constant along longitudinal axis A-A, or alternatively the width d can vary along the longitudinal axis. Varying the width d of flow channel 18 changes the shear rate characteristics of the blood moving through the member 12. This permits a single member 12 to be used to study thrombus formations under varying shear rates of blood flow.

Coatings which Produce a Blood Deposit

Within the method of the present invention, the channel has a coating which produces a blood deposit when exposed to blood. At least one of the surfaces defining the channel 18 can include a coating 25 at a concentration so as to facilitate thrombus formation in the channel 18. The coating 25 can coat all the surfaces of member 12 defining channel 18, for example, as seen in FIGS. 3A and 3B or alternatively less than all the surfaces may be coated, for example, as seen in FIG. 3C. Preferably, the transparent surface 26 is provided with the coating 25. Blood flowing through channel 18 comes in contact with and reacts with the coating 25 thereby initiating thrombus formation within the flow channel 18. The coating may be a thrombogenic material like a collagen, for example, fibrillar collagen type III or fibrillar collagen type I or alternatively, fibrinogen or a tissue factor (for example, thromborel), although any desired platelet agonists, vascular adhesive proteins, pro-coagulant, pro-inflammatory material, adhesive matrix or chemoattractant may be used. The concentration of coating 25 can depend on the material used or the extent of thrombus formation sought. For example, collagen can be used at a concentration of about 10 µg per centimeter-squared. In addition, different coatings 25 may used in combination in a single member 12 to test anti-thrombotic efficacy under varying conditions. For example, fibrillar collagen type III or I can be used to evaluate the anti-platelet agents directed against GP Ib/IX/V, collagen receptor, GPIIb/IIIa, the ADP receptor in combination with aspirin and hirudin. In another example, fibrinogen can provide information about the GPIIb/IIIa pathway and level of inhibition. In yet another example, thromborel can be used to evaluate anti-thrombotic activity of thrombin receptor antagonists. Alternatively, selectins may be used in place of or along with the coatings 25 to attract circulating cells, such as leukocytes. Alternatively, fibronectin with chemokines may be used to attract circulating cells. To test the anti-thrombotic therapy using different thrombotic agonists, member 12 can be configured to include multiple channels 18 that can run substantially parallel to axis A-A. Thus in one embodiment, the coating which produces a blood deposit is selected from a group consisting of fibrillar collagen type III, fibrillar collagen type I, fibrinogen and tissue factor. In another embodiment, said coating is human type III collagen especially wherein said subject has been administered aspirin, further comprising the addition of an ADP-receptor antagonist to the sample, wherein said concentration of said antagonist in the sample is sufficient to cause a 50% inhibition of platelet aggregation relative to a sample which has been treated with aspirin but not treated with said ADP-receptor antagonist.

Substantially Flat Transparent Housing

In one embodiment, said method uses a perfusion device further comprising a substantially flat transparent housing, wherein the channel extends through the housing with an inlet end for receiving a continuous flow of blood and an outlet end for discharging the blood. Shown in FIGS. 4I-4M is yet another example of member 12 in the form of a perfusion chamber member 12". Perfusion chamber member 12", shown in perspective view in FIGS. 4J and 4K shows an example of a substantially flat housing 54. Housing 54 can be formed of two mating portions: upper housing 56 and lower housing 58. Lower and upper housing 56, 58 portions may be joined so as to form a fluid tight seal therebetween, for example by heat sealing, joint adhesive sealing or any other techniques known to one of ordinary skill in the art for fluid tight sealing.

Lower housing 58 can be a substantially flat, housing having body 68 defining a flow channel system 18' substantially along longitudinal axis A-A through which a blood sample can be moved. In one example, channel system 18' includes a single inlet channel 40 which splits into two substantially parallel flow channels 70, 72 which terminate respectively at outlets 50, 52 coterminous with the body 68. Alternatively, flow channels 70, 72 can be configured with independent inlets. Flow channels 40, 70, and 72 define cross-sectional area 24 which may be circular, although other cross-sectional geometries are possible. Moreover, the cross-sectional geometry can vary along the longitudinal axis, for example transitioning from substantially rectangular to substantially circular along the longitudinal axis or vice versa. Flow channels 40, 70 and 72 each define a diameter d' which may vary along the channel 18' in the direction of axis A-A. Alternatively, diameter d' may be constant along the axis A-A. In addition, the dimensions or geometry of the cross-sectional area 24 of flow channels 70 can be different than the cross-sectional area of flow channel 72. Flow channels 70, 72 can be configured such that their total holding volume may be smaller than about 20 µl, although larger holding volumes can be provided for a given application. Upper housing 56 can be a substantially flat plate defining an interior surface 62 in communication with the channel system 18'.

Coating 25, as previously described, may be coated along a portion of the interior surface 62 for facilitating thrombus formation in the channel system 18' when the blood sample is moved therethrough. More specifically, the coatings 25 are applied along a portion interior surface 62 in communication with channels 70, 72 to facilitate thrombus formation therein. The coatings 25 used in, for example, flow channel 70 can be different than the coating 25 used in flow channel 72 to observe varying anti-thrombotic reactions. For example, the coating 25 in flow channel 70 may be of a different type than the coating 25 in flow channel 72, or alternatively, the coating 25 in channel 70 may vary in concentration from the coating used in channel 72. Upper housing 56 may be made from a transparent non-coating in order to facilitate the micro-videography or microscopy imaging of the thrombus formations in flow channels 70, 72.

The member 12" shown in FIG. 4K includes two substantially parallel flow channels 70 and 72. In an alternative example, as shown in FIGS. 4L and 4M, the perfusion member 12'" can include at least three flow channels 82, 84 and 86. Each flow channel 82, 84 and 86 can be separately configured in a manner similarly described with respect to flow channels 70 and 72. In addition, each channel 82, 84, and 86 can have a surface 80, 90, 92 in communication with the channel 82, 84, and 86 that is coated with varying coatings 25. Alternatively, member 12'" may be configured so as to define as many flow channels in the system of channels 18" as is needed for a blood therapy study.

Figure 2F:
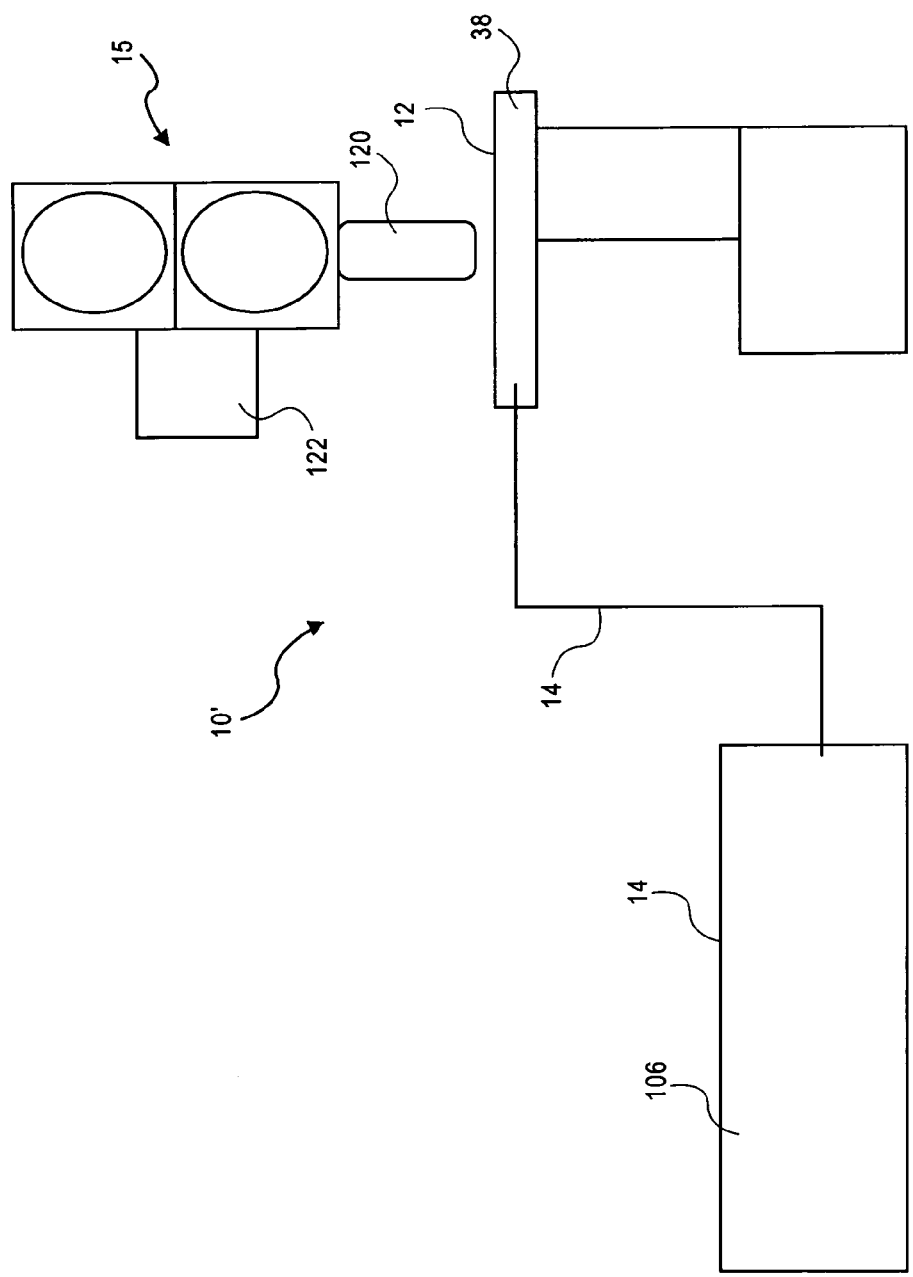
FIG. 2F is an illustration of the perfusion device of FIG. 2D.
Figure 2G:
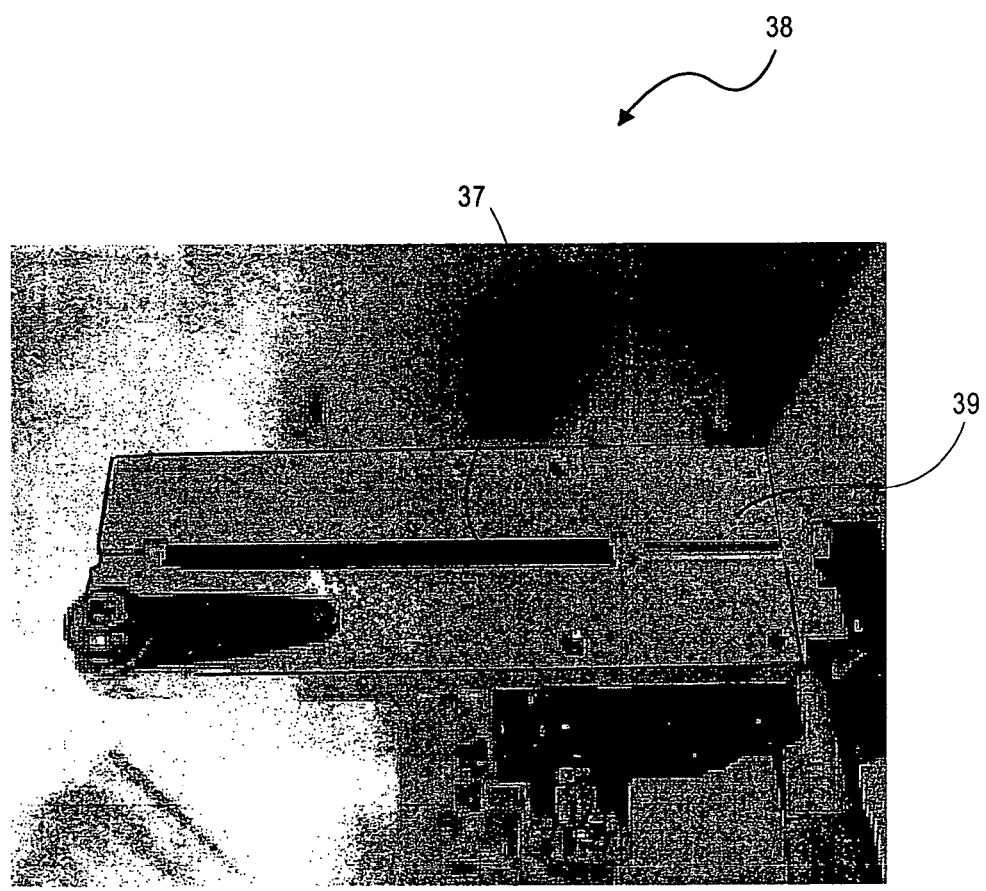
FIG. 2G is a preferred embodiment of a socket used in the perfusion device of FIGS. 2A and 2D.

Referring back to FIGS. 2C and 2F, perfusion device 10, 10' can include a receiver member or socket 38 configured for holding and orienting member 12 in a specific manner with respect to the remaining components of perfusion device 10. More specifically, socket 38 can be configured so as to properly secure and orient member 12 for proper imaging of the thrombus formations within channel 18. Socket 38 can be a holder 39 including a chamber 37 for housing the member 12 and tubing. For example, shown in FIG. 2G is another example of a holder 39 having a chamber 37 for housing the member 12. Socket 38 can be further configured to hold piping, for example, a single silastic tubing from a blood sample reservoir to the member 12 and another silastic tubing from the member 12 to the pump (not shown).

In another example, socket 38 can have a connection fitting that complementarily mates with the connection fitting of micro-capillary tube member 12 such that the transparent surface 26 is oriented with respect to imaging assembly 15 in order to image the thrombus formation inside channel 18 with the appropriate resolution and magnification. For example, socket 38 can include a telescopic stage that could be operated to bring the channel 18 into focus with respect to imaging assembly 15.

Socket 38 can be further configured so as to properly secure and orient member 12 for a liquid tight connection to the blood sample source, imaging agent source and fluid handling assembly 14. For example, socket 38 can include fluid handling fittings and elements known to one of ordinary skill in the art so as to, for example, properly deliver a blood sample or imaging agent flow channel 18. More specifically, socket 38 can include, for example, a quick disconnect coupling to permit easy and quick insertion and disconnection of member 12 from a fluid handling element of the fluid handling assembly 14, for example, a pump. In another example where member 12 can be embodied as a microchip member 12, perfusion device 10 can include a socket 38 for complimentary "snap-in" arrangement with microchip member 12, thus facilitating easy change-out of the microchip member 12 and set up of perfusion device 10 for multiple assays.

Pump and Fluid-Handling

Within the method of the present invention, the perfusion device comprises a pump which draws the blood through the channel. Referring again to the schematics of FIGS. 2A and 2D, perfusion device 10, 10' includes fluid handling assembly 14 which can have one portion 14a for handling delivery of a blood sample to member 12 and moving the blood sample through the channel 18. Fluid handling assembly 14 can have another portion 14b for handling delivery of other liquids, (not shown in FIG. 2A) for example, image enhancing agents to channel 18.

Fluid handling portion 14a can move a blood sample through channel 18 of member 12 by vacuum pressure. As seen in FIGS. 2C and 2D, fluid handling portion 14a can be single tubing, for example silastic tubing connected to inlet and outlet ends 20, 22 of member 12 to connect to the reservoir sample of blood and the syringe pump. For example, and as seen in FIG. 4I, flow channels 70 and 72 can be connected at their outlet ends 50, 52 to separate syringes 104a, 104b respectively. Syringes 104a, 104b can be conventional type syringes including pistons for creating a vacuum. Syringes 104a, 104b can be connected to a pump 106 to operate the pistons of syringes 104a, 104b. Pump 106 can be a commercially available peristaltic pump, for example, a Harvard Apparatus Pump. Additionally, fluid handling portion 14b can include tubing, valves and connection fittings to draw blood from a sample source and deposit the sample to a waste vessel upon exit from member 12. Preferably, all tubing, connections and fluid handling elements are made of non-thrombogenic material.

Fluid handling portion 14b can be configured to deliver various imaging enhancing agents to facilitate proper imaging of the thrombus formation. For example, in kinematic imaging of the thrombus formation in channel 12, preferably a fluorescent label, for example, Rhodamine 6G in saline, is added directly to the sample of blood so as to reach a concentration of about 1-20 micrograms/ml. Alternatively, the blood can be fluoresced using Mepacrine at a concentration of about 0.2 mg/ml as a dye. The dye can be added to the whole sample prior to or during perfusion. In addition, a blood sample to be kinematically imaged may be slightly anti-coagulated. The fluid handling assembly 14 can be configured to deliver a small amount of anti-coagulant, for example, PPACK, citrate, heparin, EDTA, a factor Xa inhibitor or any other anti-coagulant known in the art, to the blood sample prior to perfusion. Alternatively, the coating can be fluorescently labeled. Quenching of the fluorescent surface due to platelet deposition or an other cells becomes the read-out of the thrombobotic process.

Fluid handling portion 14b can be configured for facilitating fixed end point measurement imaging or other alternative imaging techniques to micro-videography. For example, after fluid handling portion 14a moves or perfuses a blood sample through channel 18 so as to initiate thrombus formation, fluid handling portion 14b can deliver image enhancing agents to fix and stain the thrombus formation within the channel 18 in accordance with, for example, light microscopy techniques know to one of ordinary skill in the art. Imaging enhancing agents can include: (i) a rinsing buffer; (ii) a fixing solution of either PBS or glutaraldehyde 2.5% or PBS, PFA 4%; and (iii) a stain solution, i.e. toluidin blue solution form Becton Microscopy Science. Fluid handling assembly 14 can include the requisite tubing, piping and handling elements needed for delivery of the image enhancing agents to the channel 18. In addition, a control system can be interfaced with fluid handling portion 14b to automate the sequencing and metering control of the delivery of the image enhancing agents.

Fluid handling assembly 14 can include one or more fluid control elements 100, for example, a valve that controls the flow of the blood sample into the blood sample channel 18. Any piping components, fitting and/or elements located between the blood sample reservoir and the tubing member 12 may be constructed from non-thrombogenic material and preferably constructed so as not to disturb the laminar flow of the blood sample through member 12 in order to avoid activating the platelets. These fluid control elements 100 can be configured for automatic operation by a properly interfaced control system.

Figure 4H:
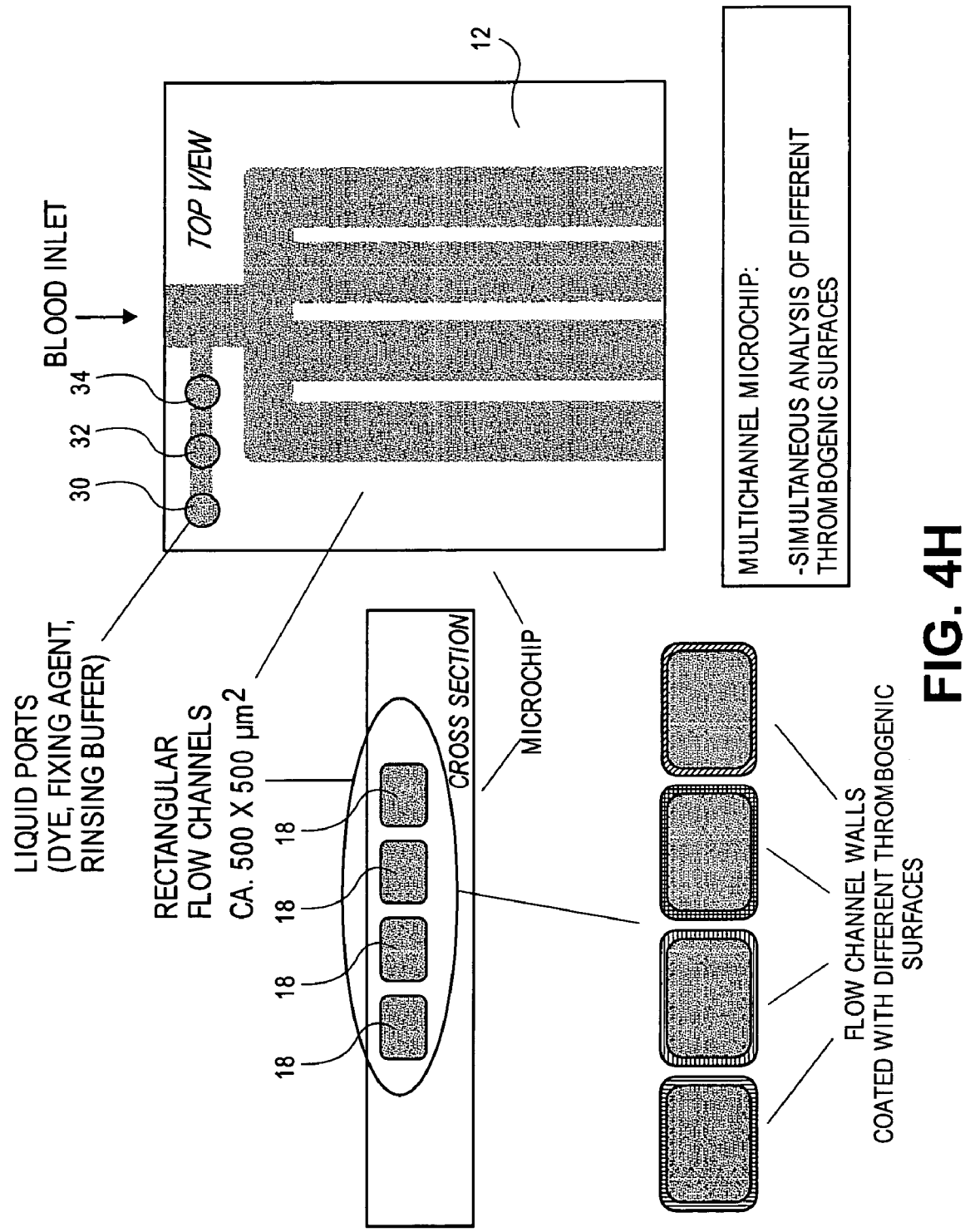
FIG. 4H are top and plan views of another example of the member in FIGS. 4E-G.
Figure 4I:
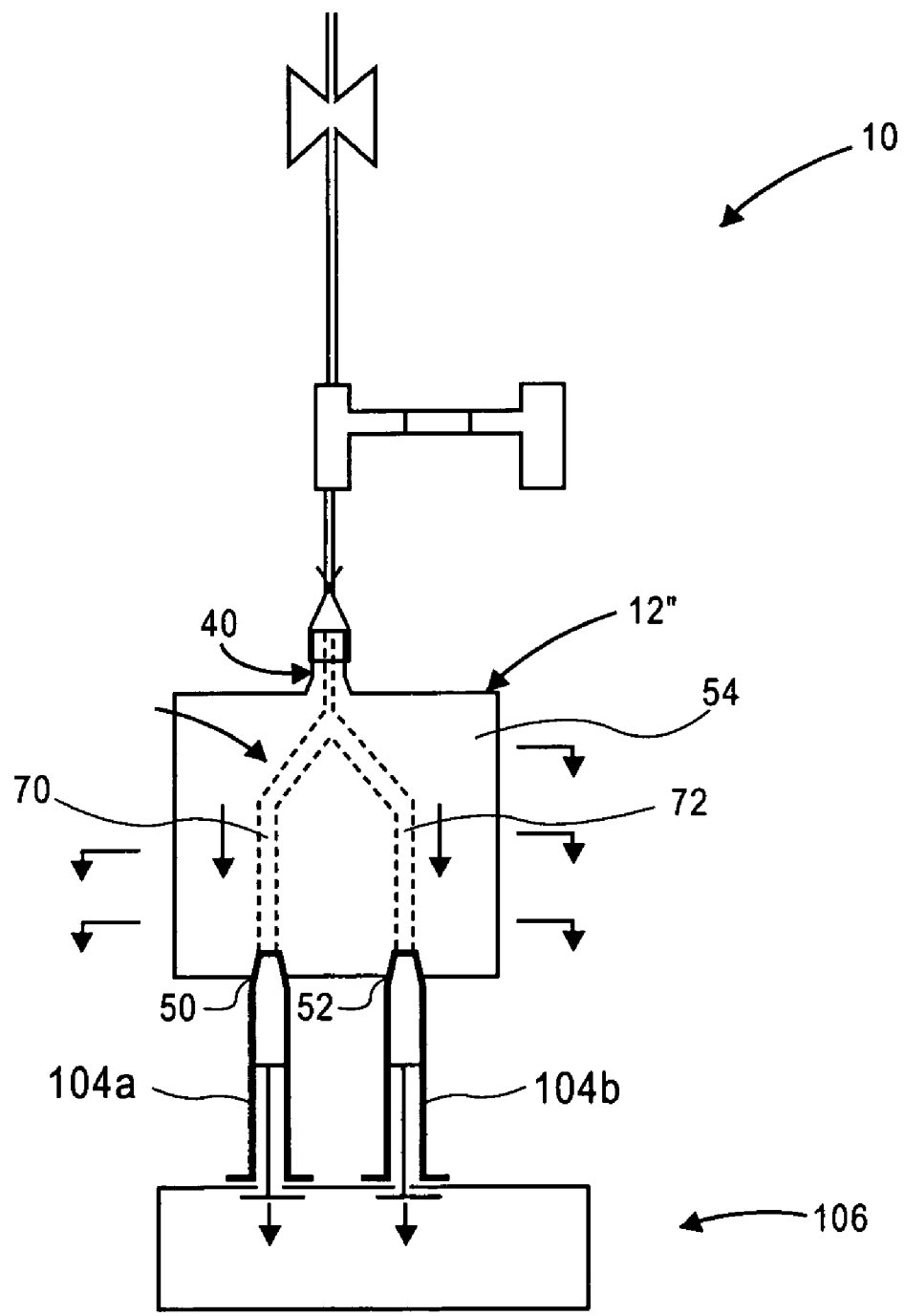
FIG. 4I-4K are plan and perspective views of another example of the member.
Figure 4J:
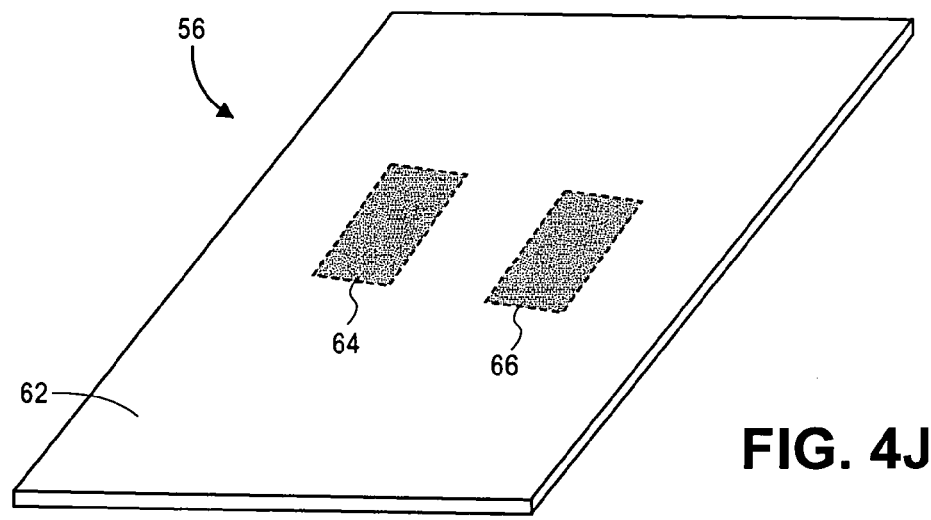
Figure 4K:
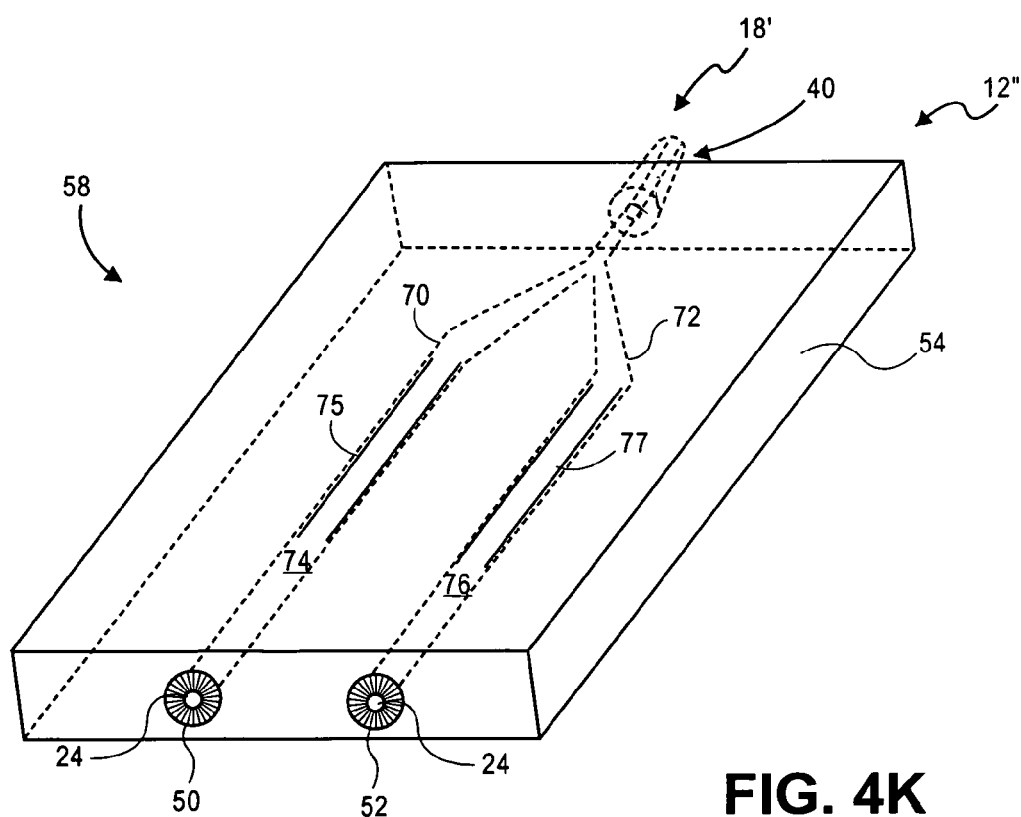
Figure 4L:
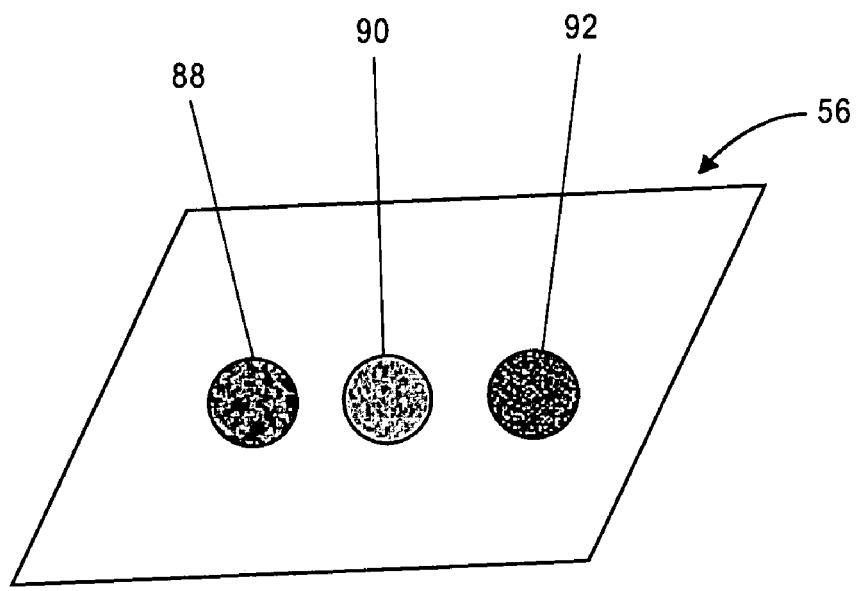
FIG. 4L-4M are perspective views of another example of the member in FIGS. 4I-4K.
Figure 4M:
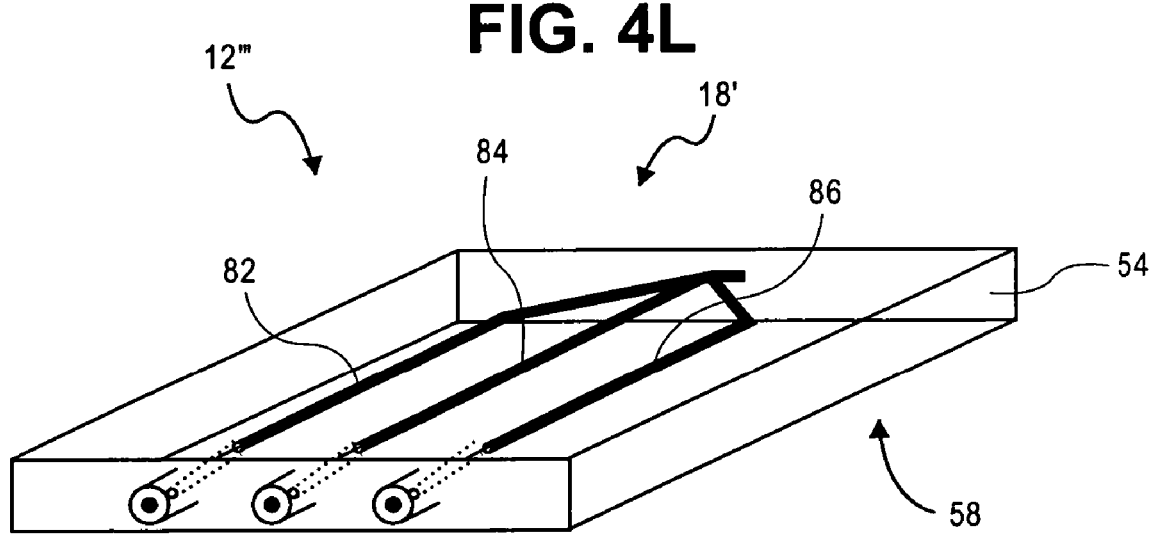

In the case of where member 12 is specifically embodied as the microchip member 12 of FIGS. 4E and 4H described above, the microchip member 12 can include fluid handling portion 14b that delivers the image enhancing agents, i.e. dye, fixing agent, rinsing buffer, etc. More specifically, microchip member 12 can include liquid ports 30, 32, and 34 of fluid handling assembly 14. Each of liquid ports 30, 32 and 34 can be configured for delivery of any one of the image enhancing agents. The liquid ports 30, 32 and 34 can be configured so as to deliver the image enhancing agents directly into the channel 18. Alternatively, the microchip member 12 can include only a single liquid port, for example, liquid port 30 to deliver all the necessary image enhancing agents.

Shear Rates

Within the method of the present invention, the pump draws the blood through the channel at a selected shear rate, producing a blood deposit. A blood sample can be moved through channel 18 of member 12 at a user selected shear rate which is expressed in units of blood per second (s−1). For example, the blood sample can be moved through channel 18 at a shear rate that mimics the human arterial shear rate estimated to be about 600 to about 800 units per second, shear rates found in moderate stenosed arteries of about 1,500 to about 10,000 units per second or alternatively mimic the human venous shear rate of about 50 to about 200 units per second. In this manner, a blood assay using perfusion device 10 can model thrombus formation in a vein or artery. In addition, the shear rate of flow through member 12 can be selected so as to account for stenosis, where a moderately stenosed artery can result in a shear rate of about 1,500 units per second, and a severely stenosed artery can result in a shear rate of about 6000 units per second.

Shear rate can be a function of both the volumetric flow rate "Q" and the cross-sectional geometry of the channel through which a fluid flows. For example, where channel 18 defines a substantially rectangular cross-sectional area 24 having a width "a" and a height "b," the shear rate at the wall shown in equation (1):

$$\gamma_{at\ wall} = 1.03 * Q/(a * b^2) \quad (1)$$

Where cross-sectional area 24 is substantially circular having a radius "r" the shear rate is found by the equation (2):

$$\gamma_{at\ wall} = 4 * Q/(\pi * r^3) \quad (2)$$

In order to regulate or adjust the shear rate to mimic blood flow through veins or arteries, the flow rate can be adjusted by accordingly changing the flow rate of the pump or otherwise changing the geometry of the channel 18. For example, as previously described, member 12 can be configured so as to vary the width d of channel 18 in the direction of flow along the longitudinal axis A-A. In one embodiment, the selected shear rate is an arterial shear rate.

Measuring the Level of Blood Deposited in the Channel

Within the method of the present invention, the status of aspirin responsiveness is determined by measuring the level of blood deposited in the channel and comparing the measured level of deposited blood with a control level of deposited blood. In one embodiment, the measurement of the rate of blood deposit comprises obtaining images of the deposited blood, and calculating the levels of deposited blood from the images, wherein said images are obtained at least once every ten seconds during perfusion.

One method of obtaining images is through use of an imaging assembly. One example of an imaging assembly is shown in FIGS. 2A and 2B. Imaging assembly 15 may be configured for kinematic imaging of the thrombus formation or recruitment of any circulating blood cells in channel 18 of member 12 using light microscopy and/or micro-videography techniques involving fluorescence illumination as is known in the art. Imaging assembly 15 of perfusion device 10 includes fluorescence excitation optics, to imaging a time-lapse video or motion picture of thrombus formation. Referring to FIGS. 2A and 2B, imaging assembly 15 of perfusion device 10 includes fluorescence excitation optics, for example, a light source 122 and a microscope 120 interfaced with a camera 124 for imaging a time-lapse video or movie of thrombus formation. Camera 124 may be a CCD camera with microscopic zoom capability to eliminate the need for a separate microscope. Camera 124 can be, for example, a Nikon DXM1200 digital camera. Camera 124 may be a digital monochrome video camera having 8-bit, integration times ca. 500 ms, IEEE1394 interface wherein images are acquired at 1-3 Hz. Microscope 120 may have for example a magnification of 20× and includes excitation and emission filters and a dichroic mirror. Light source 122 may be an LED, and more preferably, light source 122 can be a high power green LED having a preferred wavelength of about 530 nm with a narrow spectral distribution and low power consumption. Alternatively, multiple fluorescent measurements, for example using red or blue LED can be enabled to perform complex assays in which a computer controlled analyzer can support the wavelength, exposure and flow parameters of the experiment including saving the data for analysis.

Shown in FIG. 2C is an arrangement of perfusion device 10 showing relative positions of the member 12, fluid handling assembly 14, and imaging assembly 15 in an enclosure 17. The imaging assembly 15 is disposed proximate the member 12. Specifically, member 12, light source 122 and the objective of microscope 120 can be disposed relative to one another such that the light source 122 can illuminate the channel 18 and the microscope 120 can magnify and resolve the thrombus formation in channel 18 as the thrombus formation develops. The microscope 120 can be disposed relative to the transparent surface 26 of member 12 in order to focus on the thrombus formation in channel 18. The enclosure 17 is configured to substantially house the perfusion device 10 and also filter or block out surrounding room lighting so as not to interfere with the fluorescence imaging of the thrombus formation.

During perfusion of the fluorescent labeled blood sample through member 12, the blood sample reacts with the coating 25 to begin thrombus formation within channel 18. Fluorescent platelets adhere to the coated surface, thus initiating aggregation of individual platelets to form the thrombi. The imaging assembly 15 repeatedly images the thrombus formation developing in channel 18. The thrombus formation adheres and aggregates along the surfaces of channel 18 coated with coating 25. The fluorescent labeled platelets appear in the field of view of the microscope 120. The illumination from the light source 122 passing through member 12 visually enhances the view of the fluoresced thrombus formation. The lenses of the microscope 120 resolve and magnify the image of the thrombus formation with sufficient contrast so as to enable image capture and analysis of the formation.

Figure 2H:
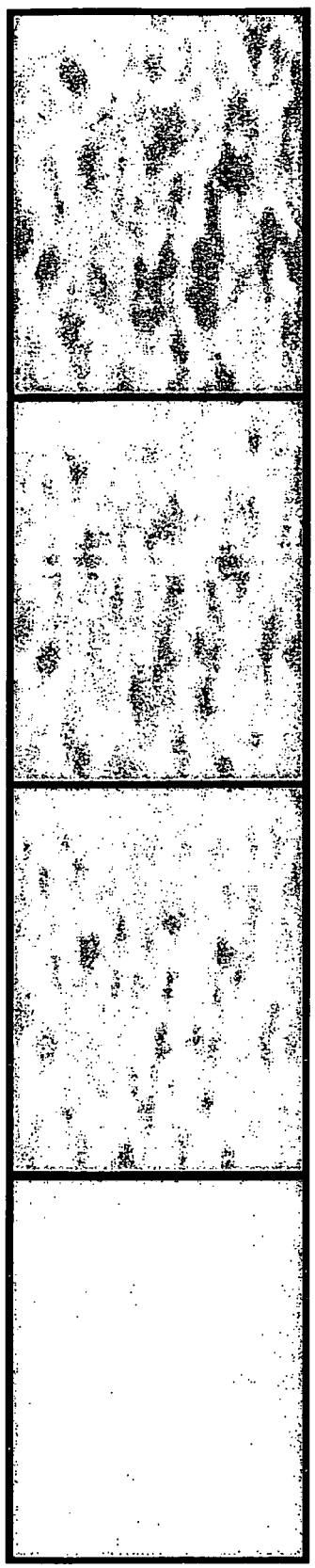
FIG. 2H is a series of still images of thrombus formations produced by the perfusion device of FIG. 2A.

The camera 124 of imaging assembly 15 captures the fluoresced image of the evolving thrombus formation as digital image data, a sample of which is shown in FIG. 2H. The frame rate of the camera 124 of imaging assembly 15 may be about 2 frames per second to capture the thrombus formation as a time-lapse motion picture. Other frame rates are possible but may require larger image data file sizes and hardware. The digital data image can be stored to read/write digital medium 137 in, for example, a hard drive of a computer or alternatively a networked data storage device.

Imaging assembly 15 can alternatively and optionally include a non-imaging photodetector 127, for example, a photodiode or photomultiplier. The photodetector 127 produces an electrical signal response to light emitted from the fluoresced thrombus formation. The electrical signal can be read, processed, and correlated by computer 136 to quantify the temporal evolution of thrombus formation and any other characteristics of the thrombus formation. The photodetector 127 can be used to provide a more sensitive, better signal to noise measurement of thrombus formation in parallel with the time-lapse video.

In addition, perfusion device 10 can be configured for performing both kinematic time lapse imaging of the thrombus formation and alternate fixed end point measurement imaging. In order to perform fixed end point measurement imaging, perfusion device 10 can be configured in a manner as described below with respect to perfusion device 10'.

Alternatively, imaging assembly 15 can be configured for fixed end point imaging of the thrombus formation in channel 18 of member 12 using light microscopy techniques and optics involving Köhler illumination as is known in the art. In contrast to the kinetic imaging of thrombus formation, fixed end point imaging captures a point in time image, the "end point" of the thrombus formation after perfusion of the blood sample through the member 12 and after the thrombus formation has been fixed and stained in the channel 18. Shown in FIG. 2D, is a schematic view of perfusion device 10' and imaging assembly 15 relative to the member 12. Preferably, imaging assembly 15 includes a light microscope 120 and a light source 122. Light source 122 may be an LED for example a high power green LED.

Figure 1:
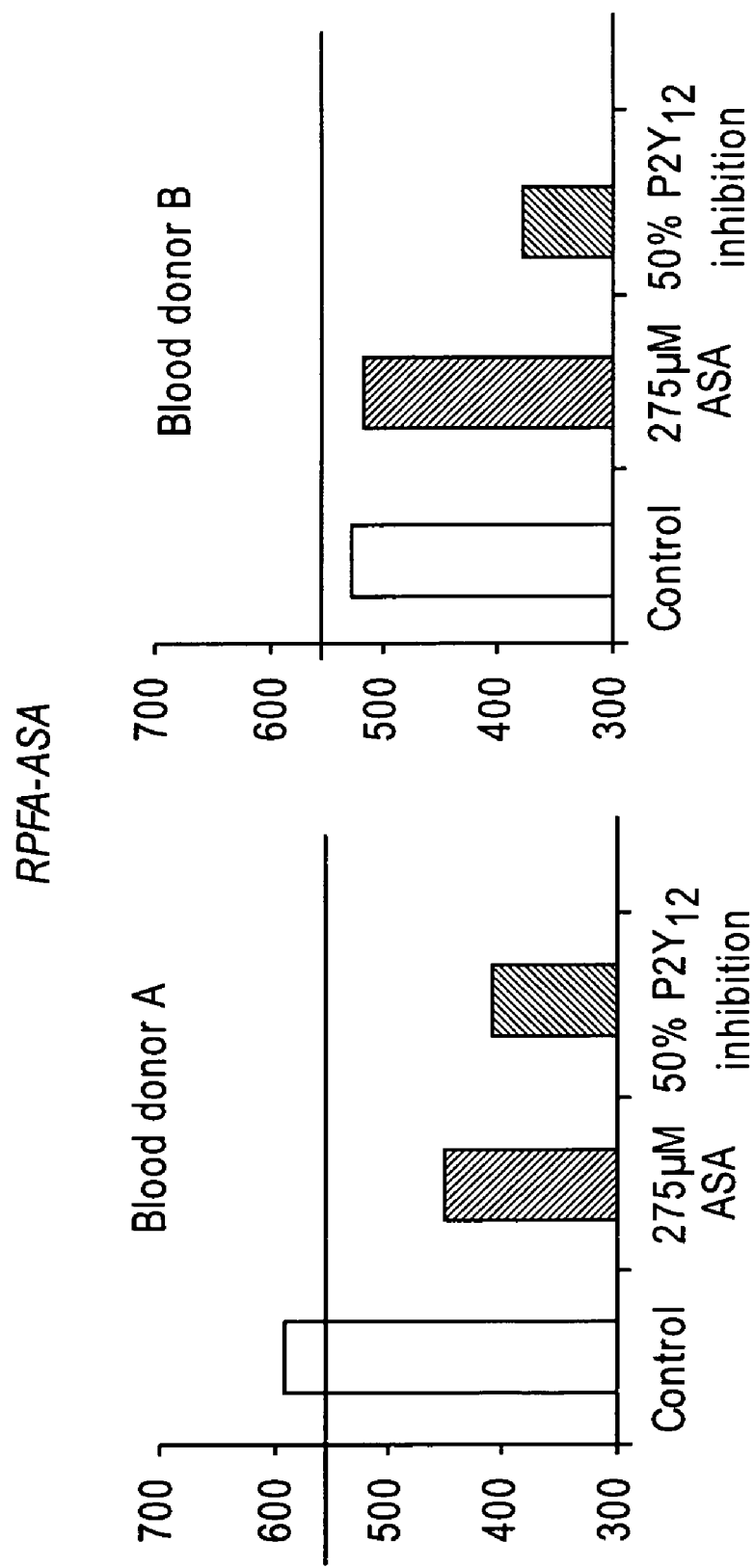
FIG. 1.

Shown in FIG. 1F is an arrangement of perfusion device 10' showing relative positions of the member 12, fluid handling assembly 14, and imaging assembly 15 in an enclosure 17. Like perfusion device 10, the imaging assembly 15 in perfusion device 10' is disposed proximate the member 12. Member 12, light source 122 and the objective of microscope 120 can be disposed relative to one another such that the light source 122 can illuminate the channel 18 and the microscope 120 can magnify and resolve the thrombus formation in channel 18 where the thrombus formation had been previously fixed and stained within the channel 18 by the image enhancing agents as previously described. In Köhler illumination, the light source 122 illuminates the fixed and stained thrombus formation. Light beams passing through the thrombus formation are refracted and captured in the object lens of the microscope 120. The lenses of the microscope 120 resolve and magnify the image of the thrombus formation with sufficient contrast so as to enable analysis of the formation.

In order to capture the image of the thrombus formation in the channel 18, imaging assembly 15 can also include a camera 124, shown schematically in FIG. 2D. More specifically, imaging assembly 15 can include a CCD camera 124 for converting the light image of the thrombus formation to a fixed digital data image. The digital data image can be stored to read/write digital medium 137 in, for example, a hard drive of a computer or alternatively a networked data storage device. As in perfusion device 10, camera 124 of perfusion device 10' can preferably include a microscopic zoom lens to eliminate the need for the separate microscope 120. Alternatively, camera 124 can be interfaced with microscope 120 to digitally capture the image of the thrombus formation.

Alternative light contrasting techniques can be employed to image the thrombus formation as are known to one of ordinary skill in the art of microscopy. Such techniques include: (i) Oblique illumination; (ii) polarization; (iii) phase contrast; and (iv) differential interference contrast.

The digital image data of thrombus formation captured by digital camera 124 in either embodiment of perfusion device 10, can be stored, displayed and printed or otherwise processed to quantify certain aspects of the thrombus formation, for example, the volume of thrombus formation. Perfusion device 10 can include an analyzer 16 having a processor 132 including an interface 134 for receiving and reading digital image and non-image data of the thrombus formation.

Processor 132 can be a computer 136 having serial connection to digital camera 124 to receive the digital image data. The camera 124 may be connected to computer 136 by a firewire connection for rapid digital image data transfer. Alternatively, computer 136 can have a disk drive as is known in the art for receiving and reading the digital image data stored to a portable read/write recording medium 125 of the camera 124. Processor 132 can convert the digital image data to pixel data in a manner known to one of ordinary skill in the art. Pixel data can include, for example, pixel color or pixel intensity. Processor 132 can further use the pixel data using at least one algorithm to correlate and/or quantify an aspect of the thrombus formation, i.e., the volume of thrombus formation.

Preferably, computer 136 can include executable software or computer program 140 capable of running the algorithm to read the digital image data and convert it to pixel data to calculate and display the quantifiable aspects of thrombus formation. The computer program 140 can be written and customized using known data acquisition software, for example, LABVIEW software. The pixel data determined by program 140 can be correlated to thrombus formation in accordance with user selected needs. For example, pixel data indicating dark colors may be correlated to indicate the presence of thrombus formation; therefore, large clusters of dark colored pixel data indicate the presence of a high concentration of thrombus formation. Alternatively, program 140 may be configured such that a cluster of light colored pixel data indicates the presence of thrombus formation. The pixel data can be used to display the image of the thrombus formation to a display device, for example, a computer monitor or for printout by a computer printer.

As previously described, perfusion device 10 and imaging assembly 15 can include a non-imaging fluorescence photodetector 127, for example, a photodiode or photomultiplier which for converting the fluorescence intensity of the platelets aggregated in the field of view to an electrical signal or other non-imaging data. In perfusion device 10, a computer 136 may be provided having software program 140 including an algorithm which can process non-imaging data received from the photodetector 127. The software program 140 can be for example, LABVIEW software including an analog to digital converter for reading the electrical signal. The software program 140 can integrate the captured fluorescence intensity over the entire field of view to give a thrombus formation curve 190 as is schematically shown in FIG. 2A. The curve 190 and its data can be further processed by program 140 to provide a temporal evolution of the volume of thrombus formation in the channel 18 and/or other quantifiable characteristics of thrombus formation.

Shown in FIGS. 2A and 2C is the analyzer 16 of FIG. 2 being a computer 136 preferably disposed proximate the imagining assembly 15 to permit immediate correlation of either (i) the digital image data or (ii) the non-imaging data as it relates to the thrombus formation. The data can be stored to the local read/write memory or hard drive of the computer 136. However, alternatively, analyzer 16 can be completely separated from the imaging assembly 15 and perfusion device 10. In one embodiment, analyzer 10 can include a stand alone computer 136 including a software or computer program 140 with at least one algorithm as previously described. Bundled detector or digital image data of blood assays can be delivered to computer 136 for analysis. For example, bundled digital data image files can be stored on a read/write recording medium 125 of imaging assembly 15 in one location and downloaded for analysis on the computer 136 in another location and stored to a data storage device or medium 137 in the same or different location. The digital image data files can be read from the portable read/write recording medium 125 using a disc drive as is known in the art. Alternatively, the digital image data files can be stored on a server 137, for example, on a local or wide area network, for example, on an intranet or the Internet. Permitting bundled data files concerning the thrombus formation to be stored for later analysis permits for high volume blood assays and imaging to be performed without having to run the thrombus formation analysis in sequence with the imaging.

Figure 5:
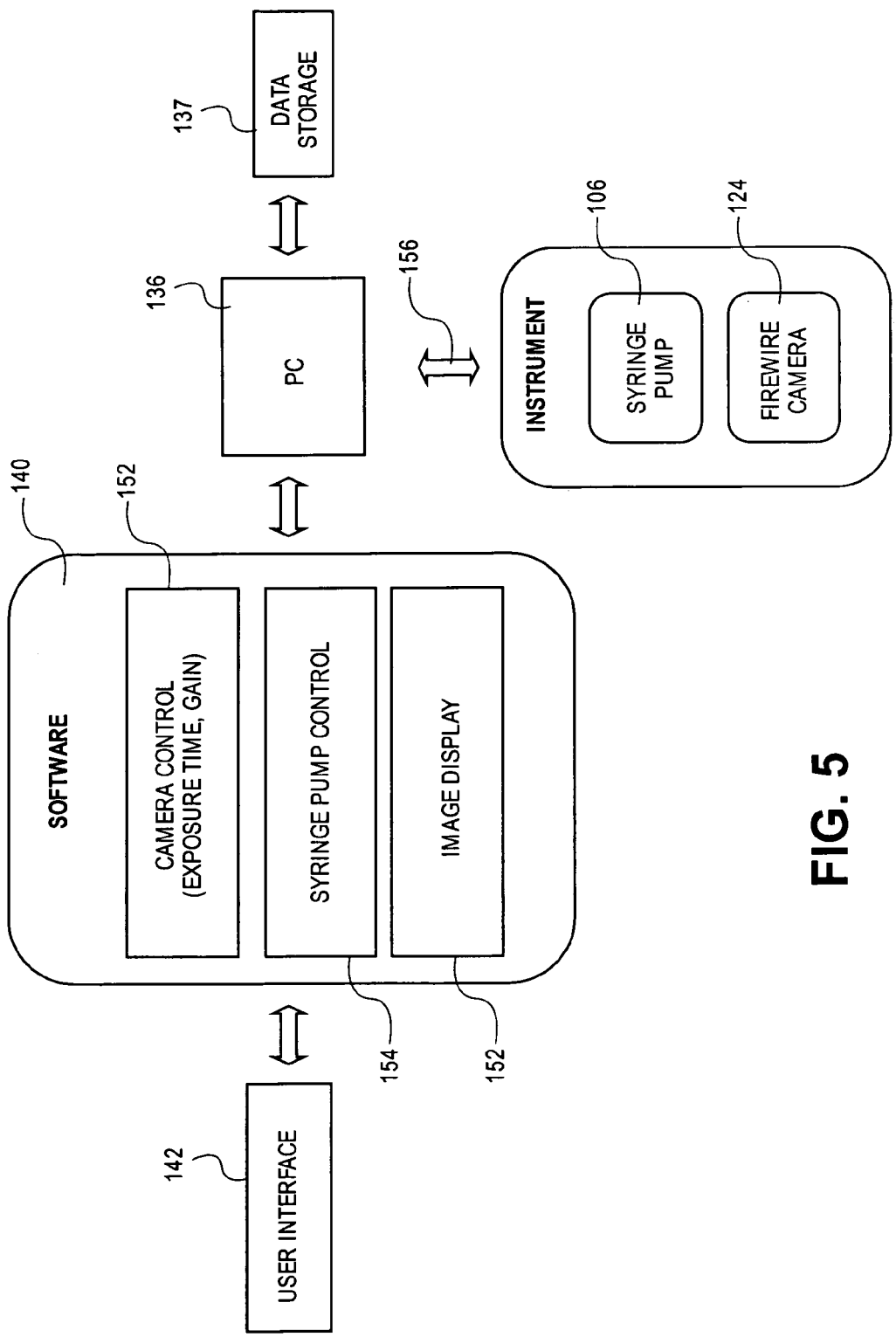
FIG. 5 is a schematic view of an a control system for use with the instruments of FIGS. 2A and 2D.

Referring now to FIG. 5, program 140 may include additional algorithms to control other features of perfusion device 10, 10' including an imaging control algorithm 152 for controlling the imaging assembly 15 and a fluid control algorithm 154 for controlling the delivery of fluids to the channel 18 of member 12 or directly to the blood sample. For example, the imaging control algorithm 152 can be configured to control the exposure times and setting of camera 124 of imaging assembly 15, wherein the computer 136 and the camera 124 preferably communicate via a firewire interface. Alternatively, algorithm 152 can be configured to control any of the previously described operations of the imaging assembly 15. In another example, the fluid control algorithm 154 can be configured to control the off/on function or the variable flow rate of pump 106. Moreover, in assays utilizing multiple channel 18 embodiments of member 12, the fluid control algorithm 154 can be configured to vary the flow parameters from channel to channel. In addition, algorithm 154 can be configured to control, for example, the sequencing or off/on delivery of the image enhancing agents used in the fluid handling assembly 14. Fluid handling assembly 14 and imaging assembly 15 can be controlled by using an appropriate interface between the computer 136 executing program 140 and its algorithms 152, 154 and the equipment to be controlled. The delivery of the image enhancing agents, in terms of either volumetric or sequential control, can be automated by a fluid control algorithm or system 154 interfaced with liquid handling assembly 14. For example, referring again to FIGS. 4E and 4H, microchip member 12 can include the requisite fluid and electrical/electronic interfaces known to one of ordinary skill in the art for connection to the blood sample source, imaging agents source, fluid handling assembly 14, or fluid control algorithm 154. It is to be understood that liquid ports 30, 32 and 34, fluid handling assembly 14 and fluid control algorithm 154 can be configured so as to deliver any agent needed for the purpose of the blood assay.

Thus to practice the methods of the present invention, a perfusion device such as perfusion device 10 can be operated in the following manner. Member 12 can be prepared by providing coating 25 on at least one of the transparent surfaces 26 defining channel 18 in order to initiate and promote thrombus formation therein. Depending on the configuration of member 12, as described above, member 12 can be pre-coated with the coating 25, for example, on the upper surface 56 of the member 12' having an adjusting tube member 60. Alternatively, member 12 can be manually coated with the coating 25 prior to running the assay, for example, using micro-capillary tube member 12. Member 12 is then assembled based upon its construction, as previously described, and inserted into the socket 38 of perfusion device 10 for secure holding and orientation relative to the remaining components of the perfusion device 10. Any necessary tubing, for example silastic tubing, is provided to connect the blood sample with the member 12 and the fluid handling assembly 14. Additionally, a rinsing buffer of, for example, a saline mixture can also be run through the tubing of perfusion device 10 to avoid air from developing in the piping system.

In one embodiment, the blood sample is treated with an anticoagulant. In another embodiment, the anticoagulant is selected from the group consisting of citrate, PPACK and heparin. If thrombus formation is imaged using kinetic or time lapse imaging of the formation, the blood sample may be labeled with a fluorescent agent and slightly anti-coagulated with a small amount of anti-coagulant, for example, heparin, Ppack, citrate, EDTA, factor Xa inhibitor or any other anti-coagulant known in the art, while in the reservoir and prior to perfusion through member 12. In other embodiments, the blood sample is not treated with an anticoagulant.

In one embodiment, fluid handling assembly 14 uses vacuum pressure to draw the fluorescent blood sample through the channel 18 of member 12. Specifically, fluid handling assembly 14 includes a syringe pump 106 having a known flow rate so as to move the sample of blood through the channel 18 having a cross-sectional area 24 of preferably known dimensions at a desired shear rate. In embodiments wherein perfusion device 10 includes a computer 136, this may include running a software program 140 including algorithm 154 in conjunction with a user interface. A user can use controls to set the flow rate of fluid handling assembly 14 or pump 106 to move the blood sample at a desired shear rate. The fluid handling assembly 14 operates to draw the blood through channel 18 of member 12 for a period of time sufficient for the blood to react with the coating in channel 18 and initiate thrombus formation in the channel 18. The period of time the fluid handling assembly 14 operates to move the blood sample through the channel 18 can be controlled by algorithm 152. In one embodiment, whole unfractionated blood is pumped through the perfusion device. In another embodiment, the rate of blood deposit is sufficient to determine the extent of aspirin responsiveness within approximately 5 minutes of the start of perfusion.

Referring back to FIGS. 2A and 2B, during perfusion of the blood sample through the member 12 and as previously described, the imaging assembly 15 repeatedly images the channel 18 at defined intervals to capture the evolving thrombus formation. Member 12 may be maintained in socket 38 of perfusion device 10 for microscopy imaging by the imaging assembly 15 in accordance with the microscopy techniques described above. Preferably, computer 136 having software program 140 including algorithm 152 and controls of user interface 142, operate the LED and preferably camera 124 including microscopic zoom lens to capture digital images of the thrombus formation under light microscopy. Alternatively, light microscope 120 is operated by computer 136 to bring the magnification and resolution of the thrombus formation into focus and coupled camera 124 captures the digital data image. The computer 136 and program 140 can additionally be configured to translate socket 38 in order to bring the thrombus formation into focus for imaging. Camera 124 can be employed with a frame rate of about 2 frames per second to capture a time-lapse image of thrombus formation. The imaging assembly 15 can take an image of thrombus formation at various points along the longitudinal axis A-A of channel 18. The time-lapse digital image data is then stored to a read/write recording medium, for example, the data storage device 137. Member 12 can then be removed from socket 38 and can be replaced by a new member 12 for running a new assay.

Once again, the user using the computer 136 having software program 140, algorithm and user interface 142 can select the digital image data files for analysis. The program 140 uses the algorithm 138 to process the digital image data so as to generate the pixel data. For each digital data image, mean pixel values, mean pixel intensities are determined and the values are displayed as outputs 146, 148. A graphic of the thrombus formation is provided in display 144 of user interface 142. The pixel data is correlated to the volume of thrombus formation and reported to the user for use in identifying and treating aspirin non-responsive patients or adjusting the anti-thrombogenic therapy.

The processor 132 or computer 136 can be configured to utilize available conventional software applications capable of reading a digital data image and converting it to visual scale data. The visual scale data can be further correlated to the quantifiable aspects of thrombus formation. For example, computer 136 can be configured to run a software application 140 capable of reading static digital image data and converting it to mean grayscale data, where the mean grayscale data is a measure of intensity or darkness of the blood sample imaged in the channel 18. Any scale can by used to measure the intensity or darkness, for example, a mean grayscale can range from zero to about 255, wherein zero is black and 255 is white. Digital image data read to have a low mean grayscale score can indicate the presence of thrombus formation. Alternatively, the grayscale may be applied inversely such that a high grayscale score indicates thrombus formation. Software application 140 can be commercially available software, for example, PHOTOSHOP™, configured to run on a processor 132 or computer 136. Alternatively, grayscale level measurements may be performed manually.

In addition or alternatively to the camera 124, a non-imaging photodetector 127 can be provided to pick up the fluorescence intensity from aggregated platelets in the channel 18 to generate an electrical signal. The signal from the photodetector 127 can be read by the computer 136 having software 140 with imaging algorithm for correlating the fluorescence non-imaging data to the temporal evolution of the volume of thrombus formation or any other temporal and quantifiable characteristic of the thrombus formation. Moreover, the user can use interface 142 to graphically display the fluorescence data correlated to the quantifiable attributes of the thrombus formation, for example such as the graph shown in FIG. 2A.

Photodetector 127 can be configured with computer 136 so as to capture time-lapse or temporal evolution images of light emitted from a thrombus formation, coagulation or any cellular movement in member 12 and display the image as a digital image data on a frame by frame basis. The imaging algorithm may be configured to read a single frame of displayed digital image data from photodetector 127 as an array of pixels, for example 1024×768 pixels, each pixel having a quantifiable pixel intensity. Because of the relative position of the photodetector 127 to the microscope objective of microscope 120 in imaging assembly 15, light emitted from the thrombus formation in member 12 and received by the photodetector 127 becomes diffused and appears as background. As a result, the imaging algorithm includes a first aspect, background or control subtraction step for removing a background or control image so as to isolate the thrombus image for quantifiable measurement.

Thus in one embodiment, the assay enables the investigator to evaluate thrombotic process under arterial shear rates in less than 15 minutes after blood draw. The simplicity of the perfusion chamber allows for multiple parallel experiments as the thrombogenic surface is deposited inside a regular glass capillary tube. The system is easy to use as only 2 tubings are needed: a proximal tubing to connect the blood sample to the capillary, and a distal tubing which connects the capillary to the pump. A limited amount of blood is required to reconstitute arterial shear rate conditions (typically 4 ml of blood for 1 perfusion chamber). Whole blood (non-anticoagulated, PPACK-, or citrate-anticoagulated human blood) can be perfused through coated capillaries at arterial shear rates for 4 minutes.

Comparing and Subtracting Control Levels

Within the method of the present invention, the status of aspirin responsiveness is determined by measuring the level of blood deposited in the channel and comparing the measured level of deposited blood with a control or threshold level of deposited blood. In certain embodiments, the control or threshold level is selected from the group consisting of (1) a level measured using a sample of blood from said subject which has been treated with aspirin; (2) a level measured using a sample of blood from said subject which has been contacted with a thromboxane A2 receptor antagonist; and (3) a level previously determined to correspond to a status of aspirin responsiveness. This comparison can be done manually as described above or the control levels may be electronically subtracted.

In subtraction step, the 1024×768 array of pixels may be divided into a subsection array of pixels, for example, a subsection array of 32×32 pixels. For each subsection of the array, a threshold value of pixel intensity is determined. This threshold value may be defined by the background intensity of the subsection array or by a previously measured value. In order to reduce or eliminate the noise content of the digital image, each subsection is subjected to a low-pass filtering process. The low-pass filter preferably includes a cut-off frequency of 30% the maximal spatial frequency contained in the image data. A threshold is determined for the low-pass filtered image of each subsection. More specifically, any pixels having an intensity of less than a given value corresponding to adherence of a platelet, for example 10, are preferably set to zero.

The imaging algorithm includes a second aspect or area calculation. Following determination of the threshold for each subsection, area calculation includes taking the balance of pixels with an intensity greater than zero and resetting their intensity value preferably to one. The sum of the pixels in the subsection array define the thrombus area in units of (pixel dimension).

The imaging algorithm includes a third aspect or volume calculation 186. Following determination of the threshold for each subsection, volume calculation 186 includes taking the balance of pixels with an intensity greater than zero and taking the summation of those intensity values to define a thrombus volume measured in (pixel dimension)2×pixel intensity. Dividing the thrombus volume by the thrombus area can provide a mean thrombus height value.

The imaging algorithm includes a fourth aspect or perimeter calculation. Following determination of the area calculation, perimeter calculation includes taking the image of pixels, each having an intensity of one, and passing it through a high-pass filtering process. The high-pass filter includes a cut-off frequency of preferably about 50% of the maximum spatial frequency contained in the threshold image. Combining the perimeter calculation with the area calculation can provide information about the shape of the thrombus formation.

In an alternative of embodiment imaging algorithm, imaging algorithm can include a first aspect or segmentation process, and second aspect or noise reduction process 184', and a third aspect or watershed separation process. Wherein photodetector 127 preferably produces a grayscale digital image data composed of pixels of varying pixel intensity, segmentation process which includes binarizing the grayscale digital image by producing a histogram for a single frame of data showing pixel intensity versus number of pixels. Taking the first derivative, second derivative or percentile method of the histogram of each image locates discrete peaks in the plot. More specifically, taking the second derivative of the initial histogram plot can reveal at least two minima points, although more are possible, wherein the first or lower minimum defining a threshold pixel intensity value. The threshold value further defines a cut-off for which pixels having an intensity less than the threshold value form the background of the digital image and the remaining foreground define the thrombus formation.

Alternative methods of computing the threshold can be utilized in which a threshold value is applied to all the images generated by the experiment. For example, the threshold value can be determined for all the images using Otsu's method (bimodal with equal variance), Kapur, Sahoo & Wong's method (1D entropy), or Abutaleb's method (2D entropy). For each of these methods, the threshold value was computed for the entire run of the experiment and then Gaussian smoothing was applied before the threshold was applied to the corresponding images.

With the threshold determined, the noise reduction process includes a first morphological operation in which small objects, for example, 5 pixels in width, that appear in the image close together, for example, within a distance of 2 pixels between each other, the objects are merged together. Next, the resultant image is subjected to a second morphological operator in which isolated voids appearing as white pixels are removed. In addition or alternatively to, small objects appearing within larger objects of the digital image data are subject to a logical operation in which pixels of the original digital image data and the digital image data produced by the first and second morphological operations are ANDed to produce a single image. The resultant image is smoothed by a median filter so as to define a final threshold mask.

The original digital image is modified by subtracting the threshold intensity value from all the pixels and applying the threshold mask to the image, thereby discarding background pixels.

The watershed separation process is applied to the resultant image, so as to identify the individual thrombi. Pixel intensity value maxima are identified and assigned a discrete color. Where discrete colors are substantially close so as to appear to merge a digital divider is located therebetween to partition the digital images of individual thrombi. The watershed is analogized to a flooding simulation. The digital image is turned upside-down, so that intensity maxima correspond to watershed minima. Modeling the image as a plastic surface, the watershed minima are imagined to define small pools in the surface with small holes in them. Imagining that the surface is submerged in water with water entering the holes such that the water level rises in the pool. Each individual pool is isolated by a dam, and anytime the pool threatens to overflow and merge with another, a dam is built to contain the overflow.

Having identified the individual thrombi, thrombus area, volume, and perimeter can be determined. For a given image, the thrombus area is obtained by counting the number of pixels forming the individual thrombi, the volume is obtained by summing the pixel intensity values for an individual thrombus, the perimeter can be obtained by counting the number of pixels that are on the edges of the thrombi. A time-lapse frame by frame plot of thrombi growth/decay can be provided by fitting the volume data to a 10th degree polynomial to display the thrombi quantities.

In an alternate method in which the thrombus formation is to be imaged using fixed end point measurement imaging, a sample of blood, preferably non-anticoagulated blood, is provided for moving through member 12. The blood sample can be drawn from a reservoir and perfused through member 12 in a manner as previously described. Alternatively, the sample of blood can be drawn directly from a person. A patient can be undergoing anti-thrombotic drug treatment and can be hooked up to the perfusion device 10 to monitor thrombosis in the patient's blood. For example, the patient can be given a dose of medication and then immediately following the dosage, blood can be perfused through system 10 to determine whether the amount of medication is appropriate. Preferably and schematically shown in FIG. 2D, fluid handling portion 14a can include the requisite tubing and fittings to draw blood from a reservoir collection vessel (not shown) in a manner well known in the art.

Once the perfusion of the blood sample through the channel 18 is complete, the thrombus formation can be fixed and stained for microscopy imaging. Preferably, fluid handling portion 14b in FIG. 2D draws imaging enhancing agents from a source (not shown). For example, the thrombus formation may be rinsed and then fixed using a solution of either PBS, glutaraldehyde 2.5% or PBS, PFA 4%. The fluid handling portion 14b can apply a toluidin blue solution to stain the thrombus formation and repeatedly rinse the channel 18 with the a rinsing buffer. The member 12 is then prepared for imaging of the thrombus formation.

Member 12 may be maintained in socket 38 of perfusion device 10 for microscopy imaging by the imaging assembly 15 in accordance with the light microscopy techniques using Köhler Illumination. As previously described, computer 136 having software program 140 including algorithm 152 and controls of user interface 142 can translate the socket 38 and operate the LED 122 and camera 124 including microscopic zoom lens or alternatively interfaced microscope 120 to focus and capture fixed end point digital images of the thrombus formation.

1. The user using the computer 136 having software program 140, algorithms and user interface 142 can select the digital image data files for analysis. The program 140 uses the digital image data in an algorithm to generate the pixel data. For each digital data image, mean pixel values, mean pixel intensities are determined and the values are displayed as outputs 146, 148. A graphic of the thrombus formation is provided in display 144 of user interface 142. The pixel data is correlated to the volume of thrombus formation and reported to the user for use in adjusting the anti-thrombogenic therapy.

In another embodiment, comparisons with control levels are done in separate experiments. Whole blood is perfused through the channels. Platelet interactions and thrombus formation are recorded in real time with the software. The mean fluorescence intensity parallels the kinetics of the thrombotic process, if platelets are labeled by a fluorescent label such as rhodamine 6G. The kinetics of the thrombotic process is recorded at 2 frames per second for 5 minutes and plotted versus time. This technique allows a physician or investigator to determine whether a drug exhibits an anti-adhesive or anti-aggregatory (platelet-to-platelet interactions) activity and its effects on thrombus stability.

Figure 10:
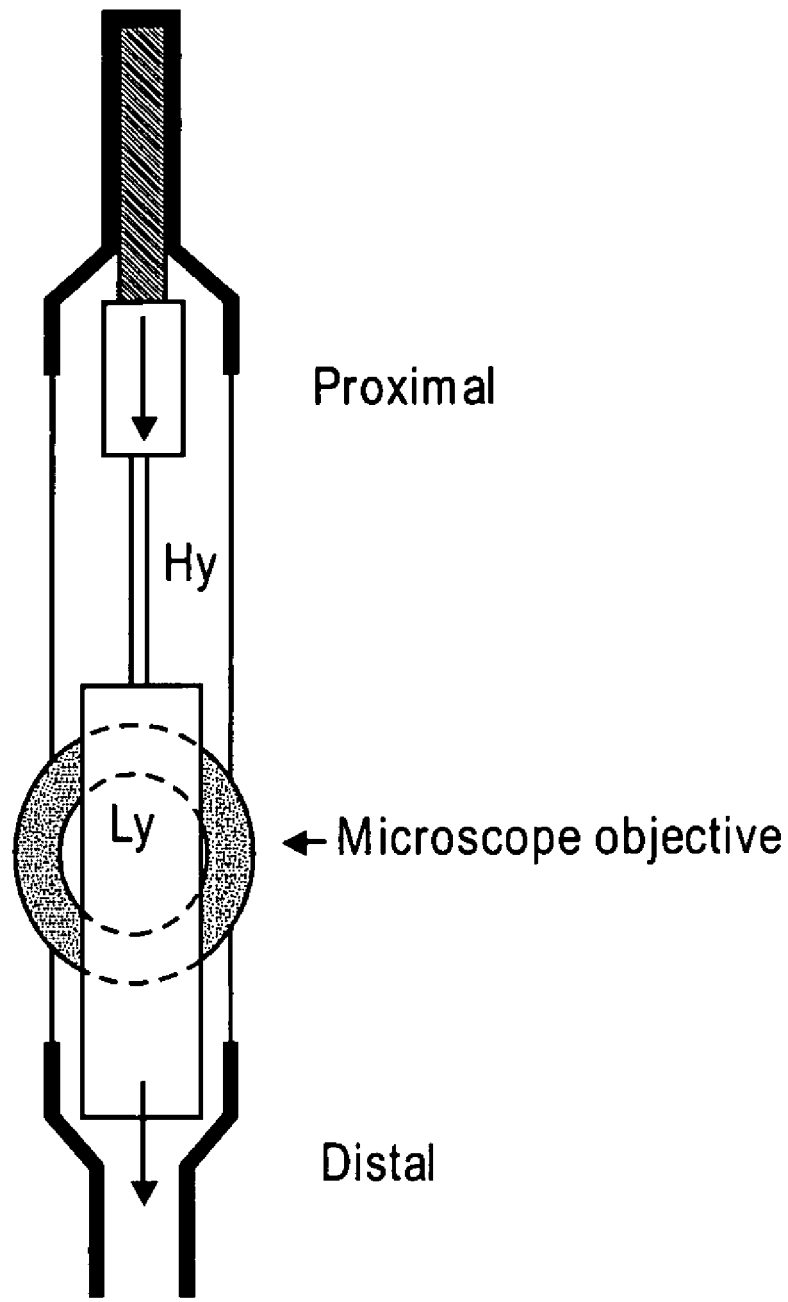
FIG. 10 is a schematic representation of the AA/shear-induced thrombotic process utilized in our preliminary study. AA (0.8 mM) is added to citrate-anticoagulated blood (37° C. incubation time=1 minute) then perfused via a silastic tubing to a stenosis (high shear rate, 1700/sec: Hγ) followed by a low shear rate area (80/sec: Lγ). Observation of the mixed platelet/leukocyte aggregates is performed under UV at 10× magnification using a fluorescent microscope.

Thus once the profiles of the platelet/leukocyte aggregates are established, the effects of aspirin can be evaluated. For example, an aspirin dose response study can be comparably performed (by addition of liquid aspirin, ASPEGIC). Similarly, other antithrombotic agents antithrombotic drugs (GP IIb-IIIa inhibitors (integrilin), direct thrombin inhibitor (Angiomax), P2Y12 antagonism (5-chloro-N-[({4-[7-fluoro-6-(methylamino)-1-oxoisoquinolin-2(1H)-yl]phen- yl}amino) carbonyl]thiophene-2-sulfonamide)) can be evaluated in order to obtain a mean thrombotic profile for each treatment. This method can also be tested with blood treated with combinations of treatments such as $P2Y_{12}$ inhibitor+epinephrine, in the presence or absence of aspirin. A schematic representation of the chamber (Aspirin-Chip) is shown in FIG. 10.

Thus in one embodiment, the perfusion device provides real time measurements of (1) the thrombotic profile of aspirin effects on top of $P2Y_{12}$ antagonism in a collagen-coated perfusion chamber assay under arterial shear rates and (2) arachidonic acid/shear-induced platelet aggregation assay in whole blood under high shear rates.

In another embodiment, the invention described herein provides a method for utilizing a single apparatus that will evaluate: 1) the thrombotic profile of aspirin effects on top of $P2Y_{12}$ antagonism in a collagen-coated perfusion chamber assay under arterial shear rates; 2) arachidonic acid/shear-induced platelet aggregation assay in whole blood also under high shear rates. One main advantage of this technique is that it will enable the investigator to assess the variability of the aspirin resistant phenotype and its dose dependence. A lack of efficacy of aspirin in both assays will be correlated with aspirin resistance. A major limitation of the PFA-100 device as well as classical perfusion chambers is the lack of real time qualitative assessment of both platelet adhesion and thrombus formation. Another advantage of this technique is that it is insensitive to the presence of therapeutic amounts of platelet ADP-receptor antagonists in the subject's bloodstream. Thus in another embodiment, the method is insensitive to the presence of therapeutic amounts of platelet ADP-receptor antagonists in the subject's bloodstream.

Methods of Treatment/Administration

One aspect of the present invention is identifying subjects with aspirin resistance so that they qualify for treatment with a thromboxane A2 receptor antagonist. Thus in one embodiment, the present invention provides a method of qualifying a subject for treatment with a thromboxane A2 receptor antagonist, comprising:

(a) perfusing a blood sample from said subject through a channel in a perfusion device, wherein the channel has a coating which produces a blood deposit when exposed to blood and the perfusion device comprises a pump coupled to the outlet end of the housing to draw the blood through the channel at a desired shear rate, producing a blood deposit, and wherein said blood sample is treated with an amount of a platelet ADP receptor antagonist sufficient to inhibit thrombosis at least approximately 20% relative to an untreated sample; and (b) wherein said blood sample is treated with an amount of aspirin sufficient to cause at least an approximately 50% inhibition of thrombosis in a blood sample relative to an untreated sample; and (c) wherein a subject is qualified for treatment with a thromboxane A2 receptor antagonist if less than approximately 50% inhibition of thrombosis is observed in said blood sample relative to an untreated sample.

Once a subject has been identified as an aspirin non-responder using the above methods, they may be treated with a thromboxane A2 receptor antagonist, either alone or in combination a platelet ADP-receptor antagonist. Examples of thromboxane A2 receptor antagonists include but are not limited to Terbogrel, Ridogrel, Ramatroban, Seratrodast, Ozagrel, Ifetroban, BM-531 and S18886. Examples of platelet ADP-receptor antagonists include, but are not limited to PLAVIX (clopidogrel bisulfate). Preferably, the platelet ADP-receptor antagonist is PLAVIX (clopidogrel bisulfate). Methods for preventing or treating thrombosis in a mammal by administering to the mammal a therapeutically effective amount of these compounds, alone or as part of a pharmaceutical composition of the invention as described above can be done following procedures known to those of skill in the art.

The methods of the invention may be utilized in vivo, ordinarily in mammals such as primates, (e.g., humans), sheep, horses, cattle, pigs, dogs, cats, rats and mice, or in vitro.

Subjects (typically mammalian) in need of treatment by the methods of the invention may be administered dosages that will provide optimal efficacy. The dose and method of administration will vary from subject to subject and be dependent upon such factors as the type of mammal being treated, its sex, weight, diet, concurrent medication, overall clinical condition, the particular compound employed, the specific use for which the compound or pharmaceutical composition is employed, and other factors which those skilled in the medical arts will recognize.

Therapeutically effective dosages may be determined by either in vitro or in vivo methods. For each particular compound or pharmaceutical composition of the invention, individual determinations may be made to determine the optimal dosage required. The range of therapeutically effective dosages will be influenced by the route of administration, the therapeutic objectives and the condition of the patient. For injection by hypodermic needle, it may be assumed the dosage is delivered into the bodily fluids. For other routes of administration, the absorption efficiency must be individually determined for each compound by methods well known in pharmacology. Accordingly, it may be necessary for the therapist to titer the dosage and modify the route of administration as required to obtain the optimal therapeutic effect.

The determination of effective dosage levels, that is, the dosage levels necessary to achieve the desired result, i.e., platelet ADP receptor inhibition, will be readily determined by one skilled in the art. Typically, applications of a compound or pharmaceutical composition of the invention are commenced at lower dosage levels, with dosage levels being increased until the desired effect is achieved. The compounds and compositions of the invention may be administered orally in an effective amount within the dosage range of about 0.01 to 1000 mg/kg in a regimen of single or several divided daily doses. If a pharmaceutically acceptable carrier is used in a pharmaceutical composition of the invention, typically, about 5 to 500 mg of a compound is combined with a pharmaceutically acceptable carrier as called for by accepted pharmaceutical practice including, but not limited to, a physiologically acceptable vehicle, carrier, excipient, binder, preservative, stabilizer, dye, flavor, etc. The amount of active ingredient in these compositions is such that a suitable dosage in the range indicated is obtained.

In another embodiment the aspirin non-responder is a subject having an aspirin responsiveness of less than or equal to 50% of the value for aspirin responsiveness. Thus in one embodiment, the present invention provides a method of treating an aspirin non-responsive subject comprising:

(a) identifying a subject as an aspirin non-responder using any of the above methods, wherein an aspirin non-responder is a subject having an aspirin responsiveness of less than or equal to 50% of the value for aspirin responsiveness; and (b) administering to the aspirin non-responsive subject a thromboxane A2 receptor antagonist. In another embodiment, the thromboxane A2 receptor antagonist is selected from the group consisting of Terbogrel, Ridogrel, Ramatroban, Seratrodast, Ozagrel, Ifetroban, BM-531 and S18886. In another embodiment, the present invention provides a method of treating an aspirin non-responsive subject comprising the steps of:

identifying a subject as an aspirin non-responder according to any of the above methods; and administering to the subject a thromboxane A2 receptor antagonist in combination with a platelet ADP-receptor antagonist. In one embodiment, the thromboxane A2 receptor antagonist is selected from the group consisting of Terbogrel, Ridogrel, Ramatroban, Seratrodast, Ozagrel, Ifetroban, BM-531 and S18886. In another embodiment, the platelet ADP-receptor antagonist is selected from the group consisting of PLAVIX (clopidogrel bisulfate). In another embodiment, the platelet ADP-receptor antagonist is PLAVIX (clopidogrel bisulfate).

The following examples are offered by way of illustration only and are not intended to limit the scope of the claimed invention. Numerous embodiments of the invention within the scope of the claims that follow the examples will be apparent to those of ordinary skill in the art from reading the foregoing text and following examples.

EXAMPLES

Example 1

Evaluation of RPFA-ASA and PFA-100

The effects of aspirin (275 µM added to the blood in vitro) and 50% inhibition of $P2Y_{12}$ (corresponding to the extent of inhibition achieved in patients under PLAVIX (clopidogrel bisulfate) treatment) were evaluated in the RPFA-ASA (n=5). A direct $P2Y_{12}$ antagonist (5-chloro-N-[({4-[7-fluoro-6-(methylamino)-1-oxoisoquinolin-2(1H)-yl]phenyl}amino)carbonyl]thiophene-2-sulfonamide) is used in vitro at a concentration that inhibits 50% of ADP-induced platelet aggregation in PRP as PLAVIX (clopidogrel bisulfate) cannot be used in vitro (it needs to be metabolized by the liver to generate the active metabolite). The results show that aspirin effects were smaller than that obtained with 50% inhibition of $P2Y_{12}$ (FIG. 1, blood donor A and B) for all 5 blood donors. Also, one donor presented an aspirin-like phenotype without addition of aspirin or aspirin uptake (donor B). Since the actual anti-platelet regimen consists of a combination of aspirin and $P2Y_{12}$ antagonist, the RPFA-ASA assay cannot detect aspirin response on top of $P2Y_{12}$ inhibition.

Figure 6:
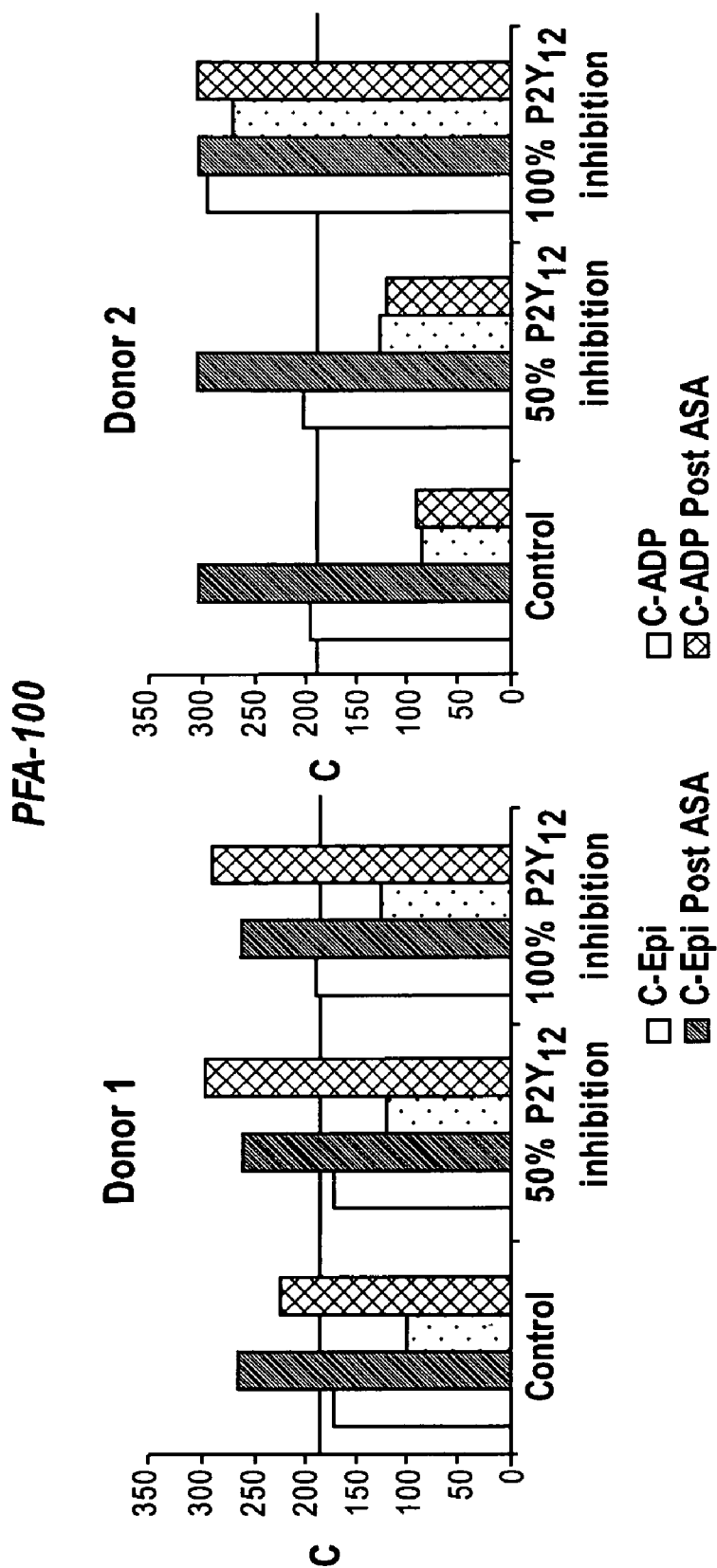
FIG. 6 shows the effects of aspirin and 50% inhibition of P2Y$_{12}$ on arachidonic acid-induced platelet aggregation in PRP, TxB2 generation using PFA-100 with both Collagen/Epinephrine (CEpi) and Collagen/ADP (CADP) cartridges. Whole blood was drawn into 3.8% Sodium citrate vacuum tubes and analyzed using the Platelet Function Analyzer (PFA-100). Sample results are based on the platelet function under high shear stress. Platelet adhesion and aggregation are triggered by a biologically active membrane coated with collagen and either epinephrine (EPI) or ADP. Platelets exposed to EPI or ADP under flow conditions are activated on the collagen surface. The time required to full occlusion of an aperture cut in the membrane defines the "closure time" (CT).

The effects of aspirin (normal volunteers were drug free for 2 weeks prior to 325 mg/d ASA for 3 days) and 50% inhibition of $P2Y_{12}$ on arachidonic acid-induced platelet aggregation in PRP, TxB2 generation, PFA-100 with both Collagen/Epinephrine (CEpi) and Collagen/ADP (CADP) cartridges were evaluated. Arachidonic acid-induced platelet aggregation and TxB2 generation were abolished by aspirin treatment compared with baseline for all 5 donors. In the PFA-100 model, the effect of aspirin is revealed by an increase in closure time in the CEpi cartridge, with an unchanged value for the CADP cartridge. All donors gave the expected prolongation of the CEpi cartridge after aspirin treatment. In addition, 2 out of 5 donors presented unusual phenotypes (FIG. 6). In donor 1, aspirin increased the CADP closure time, whereas in donor 2, $P2Y_{12}$ antagonism increased closure time of the CEpi cartridge above the limit defined by the manufacturer for aspirin effect.

These preliminary studies highlight differences in the platelet monitoring devices in a normal population with both RPFA-ASA and PFA-100, and may likely be more variable in clinical studies with patients, potentially leading to multiple misinterpretations. In addition, none of the assays gave a qualitative real time measurement of the thrombotic process to reveal full or partial inhibitory effects of aspirin in vivo. Finally, whether the PFA-100 correlates with future clinical events is uncertain (Gum, P. A. et al., *J Am Coll Cardiol*, 41(6):961-5 (2003)).

Example 2

Perfusion Chamber Assays

In one example of the perfusion chamber assay of the invention, the assay enables the investigator to evaluate thrombotic process under arterial shear rates in less than 15 minutes after blood draw. The simplicity of the perfusion chamber allows for multiple parallel experiments as the thrombogenic surface is deposited inside a regular glass capillary tube. The system is easy to use as only 2 tubings are needed: a proximal tubing to connect the blood sample to the capillary, and a distal tubing which connects the capillary to the pump. A limited amount of blood is required to reconstitute arterial shear rate conditions (4 ml of blood for 1 perfusion chamber). Whole blood (non-anticoagulated, PPACK-, or citrate-anticoagulated human blood) is perfused through fibrillar type III collagen-coated capillaries at arterial shear rates for 4 minutes.

Figure 7:
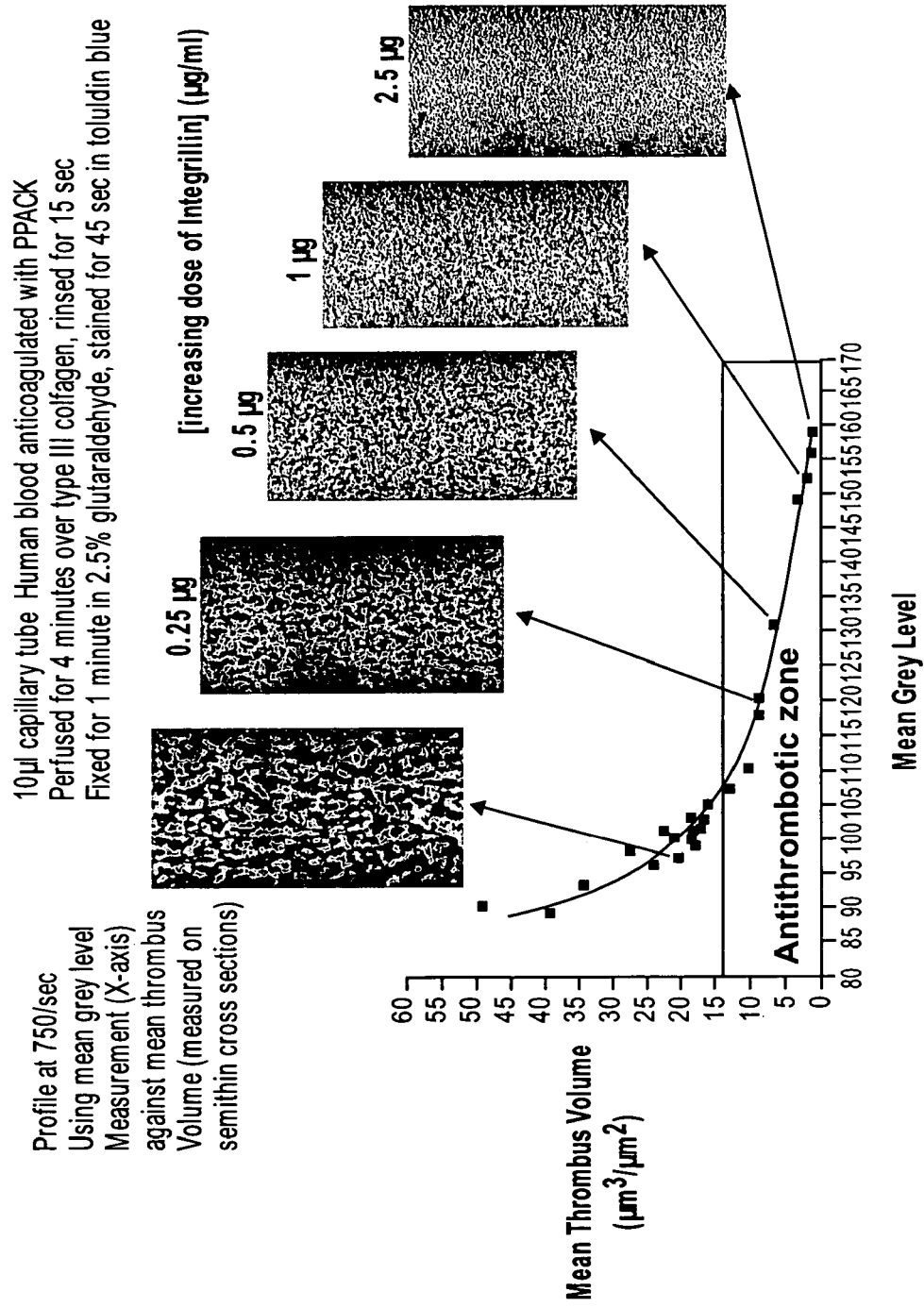
FIG. 7 shows a thrombotic profile in the perfusion chamber. Mean thrombus volumes quantified on semi-thin cross sections were plotted against their corresponding mean grey levels using Prism Software. The top of the figure corresponds to cross sections performed inside the 400×250 μm rectangle that was analyzed for the mean grey level at 5 mm from the proximal part of the capillary. Capillary chambers were perfused with either PPACK-anticoagulated blood treated with increasing doses of Eptifibatide (Integrilin) at 750/sec (empty squares), or with non-anticoagulated blood at 1500/sec (black squares). Bar=120 μm. Double bar=100 μm. The sole measurement of the grey level is now performed to determine mean thrombus volume.

At the end of the perfusion, the capillary is rinsed for 20 sec and fixed with 2.5% phosphate buffered glutaraldehyde for 1 minute. Capillaries are stained for 45 sec with toluidine blue, then rinsed with buffer "C". An En Face picture located 5 mm downstream of the proximal part of the capillary is taken, and the grey level of each thrombus or platelets located in a window 400 µm long×400 µm wide is measured (Simple PCI software, Compix Inc. Imaging System). Thrombotic deposits were then embedded in Epon, subsequently cross sectioned (at the same location used for measurement of the grey level) and their mean thrombus volume determined. Mean grey level is then plotted against the corresponding mean thrombus volume. A thrombotic profile curve is obtained by titrating with the GP IIb-IIIa antagonist eptifibatide (FIG. 7). The same profile can be generated for the rectangular perfusion chamber and utilized for a rapid measurement of the effects of different drugs on the arterial thrombotic process.

Using this technique, the antithrombotic effects of aspirin and $P2Y_{12}$ inhibitors are observed to synergize on collagen. The same technique may be used to show that $P2Y_{12}$-deficient mice are protected from vascular occlusion following $FeCl_3$ injury of mesenteric arteries. This phenotype is rescued by the injection of epinephrine in vivo (Andre, P. et al., *J Clin Invest*, 112(3):398-406 (2003)). Similarly, epinephrine was able to correct the phenotype of $P2Y_{12}$-deficient mice in a collagen-coated perfusion chamber (epinephrine stimulates the Gz pathway that compensates for the blockade of the $P2Y_{12}$-coupled Gi pathway).

Example 3

Collagen-Coated Perfusion Chamber Assay to Measure Aspirin Resistance in Whole Blood.

Platelets are labeled in whole blood with Rhodamine 6G and used to show that aspirin and thrombin inhibitors synergize with $P2Y_{12}$ antagonism (Andre, P. et al., *Circulation*, 108(21):2697-703 (2003)). After blood collection into either citrate or PPACK (4 ml are needed per perfusion chamber) Rhodamine 6G (0.2 mg/mL) is added to the blood and incubated at 37° C. for 5 minutes. Collagen-coated rectangular glass capillaries (Vitrocom) are mounted on the stage of a fluorescent microscope and illuminated under light, UV, or both. Whole blood is perfused at 1000/sec through the capillaries. Platelet collagen interactions and thrombus formation are recorded in real time with the Simple PCI software. The mean fluorescence intensity parallels the kinetics of the thrombotic process, because all platelets are labeled by rhodamine 6G. The kinetics of the thrombotic process is recorded at 2 frames per second for 5 minutes and plotted versus time. This technique allows a physician or investigator to determine whether a drug exhibits an anti-adhesive or anti-aggregatory (platelet-to-platelet interactions) activity and its effects on thrombus stability. Experiments are performed with different antithrombotic drugs (GP IIb-IIIa inhibitors (integrilin), direct thrombin inhibitor (Angiomax), $P2Y_{12}$ antagonism (5-chloro-N-[({4-[7-fluoro-6-(methylamino)-1-oxoisoquinolin-2(1H)-yl]phenyl}amino)carbonyl]thiophene-2-sulfonamide)) and notably aspirin in order to obtain a mean thrombotic profile for each treatment. This method is then tested with blood treated with $P2Y_{12}$ inhibitor+epinephrine, in the presence or absence of aspirin.

Most ACS patients eligible for percutaneous coronary intervention (PCI) are under PLAVIX (clopidogrel bisulfate) therapy. Since the level of $P2Y_{12}$ inhibition varies in patients (depending on the loading doses of PLAVIX clopidogrel bisulfate) and the time of administration) a full blockade of the $P2Y_{12}$ receptor is achieved with 5-chloro-N-[({4-[7-fluoro-6-(methylamino)-1-oxoisoquinolin-2(1H)-yl]phenyl}amino)carbonyl]thiophene-2-sulfonamide, a direct $P2Y_{12}$ inhibitor, in vitro. $P2Y_{12}$ antagonism is overcome by stimulation of the G protein z (Gz) pathway with epinephrine added to the whole blood prior to perfusion. This reveals the aspirin antithrombotic activity in all patients. Trisodium citrate is used in this example as anticoagulant because it reveals aspirin effects in perfusion chamber assays (Baumgartner, H. R. et al., Thromb Haemost, 35(1): 124-38 (1976)).

Fibrillar type III collagen has been chosen in this example for the thrombogenic material as the effects of aspirin can be observed in perfusion chambers coated with fibrillar collagen under arterial shear rate conditions. In addition, increased responsiveness to collagen has been proposed to contribute to aspirin resistance (Zimmermann, N. et al., J Thorac Cardiovasc Surg, 121(5):982-4 (2001); Kawasaki, T., et al., Stroke, 31(3):591-5 (2000)). Preparation of type III fibrillar collagen requires dialysis against phosphate buffer for 40 hours. Therefore, collagen Horm (a mixture of different fibrillar collagens) can be used as alternative in this system since it is commercially available and does not require extensive preparation for coating.

Volunteers from a blood donor program can be used to firmly establish the concentration of epinephrine needed for correction of the $P2Y_{12}$ antagonism and to evaluate aspirin effects on $P2Y_{12}$ antagonism+epinephrine background.

Figure 8:
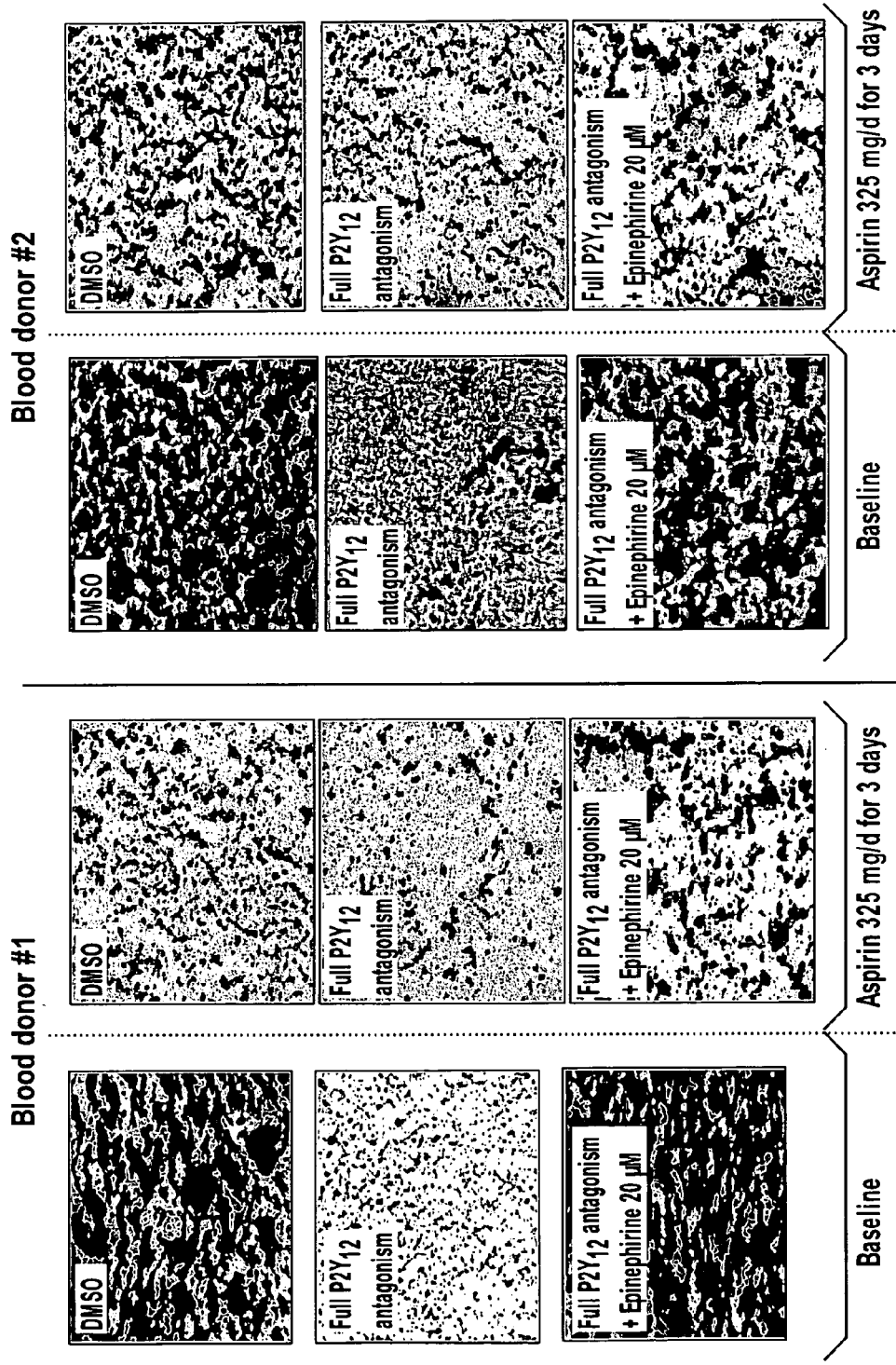
FIG. 8A shows representative pictures of the thrombotic process forming in the rectangular perfusion chamber at different time points. Phe-Pro-Arg-chloromethylketone (PPACK)-anticoagulated blood is added to a tube containing Rhodamine 6-glucose (Rhodamine 6G) (0.2 mg/ml). Five minutes later, blood is perfused through a rectangular capillary mounted on the stage of an inverted microscope (under ultraviolet (UV) light (Rhodamine filter) platelets appear fluorescent). As the blood flows on the collagen type III-coated capillary chamber, platelets adhere and start building a thrombus. Two frames per second are recorded and analyzed for mean fluorescent intensity for the entire perfusion period. At the end of the perfusion, standard deviation in light intensity is plotted against the time by the Prism software.
FIG. 8B represents the thrombotic profiles of untreated or Integrilin-treated blood (flat curve).

FIG. 8 shows the real time kinetics of thrombus formation in a perfusion chamber perfused with either untreated PPACK-anticoagulated blood (black circles and black line) or 2.5 μM Integrilin (GP IIb-IIIa antagonist)-treated PPACK-anticoagulated blood.

Figure 9:
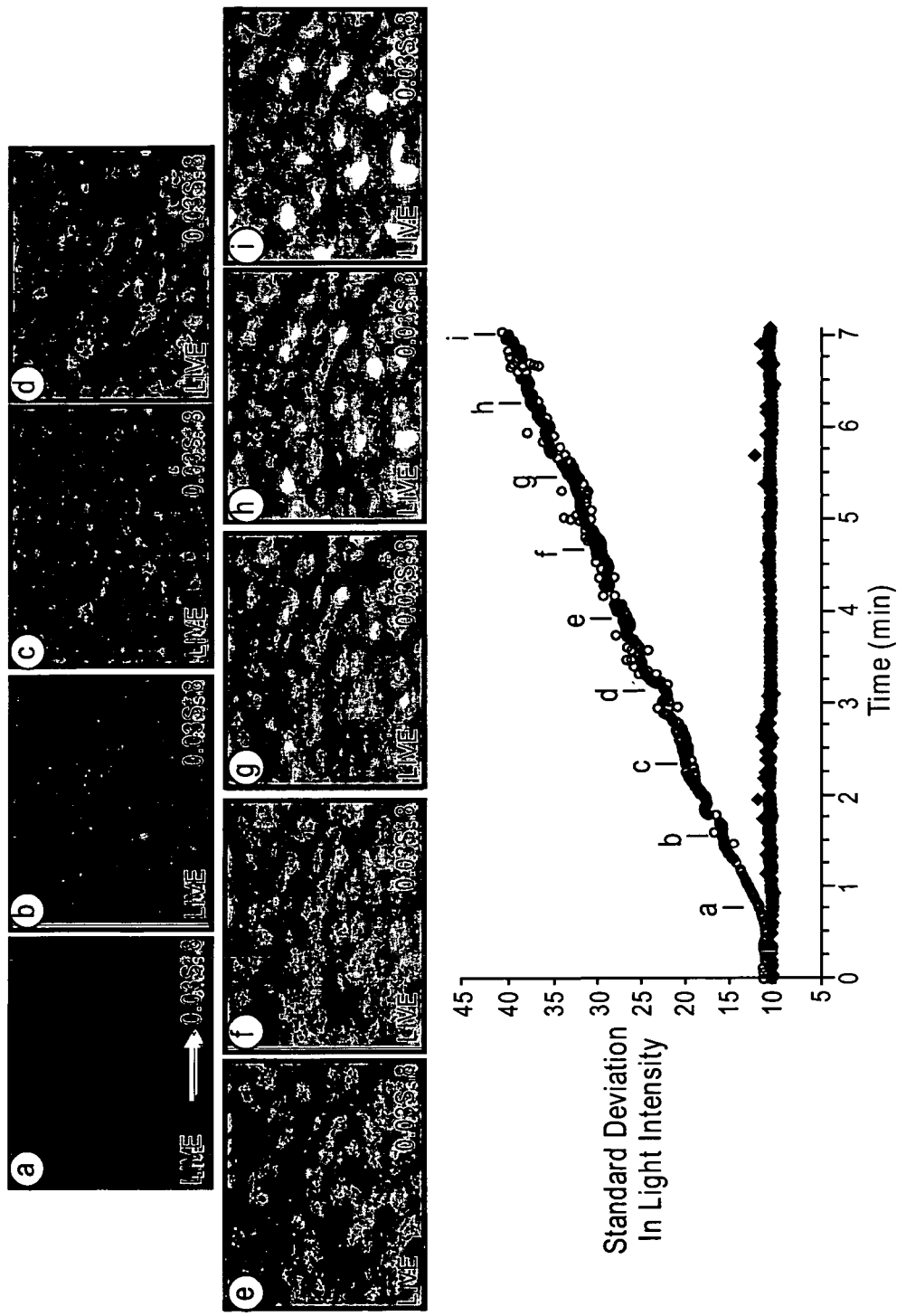
FIG. 9 is a representation of the thrombotic deposits formed on type III collagen at 1000/sec in the rectangular perfusion chamber in 2 blood donors, before and after aspirin uptake (325 mg/d for 3 days). Anticoagulated blood (citrate 3.8%, 1:9 v of blood) is collected and added into 5 ml tubes containing either DMSO (vehicle control for the $P2Y_{12}$ antagonist), a direct $P2Y_{12}$ antagonist at 5 μM (which totally block the receptor), or a direct $P2Y_{12}$ antagonist at 5 μM in presence of 20 μM Epinephrine. Anticoagulated blood is perfused through a rectangular capillary (0.2×2 mm, Vitrocom) coated with fibrillar type III collagen at 1000/sec for 4 minutes. Thrombotic deposits are then rinsed for 15 seconds with buffer "C", fixed for 1 minute in phosphate-buffered glutaraldehyde (2.5%), stained for 45 sec in toluidine blue. Picture is taken at 5 mm from the proximal part of the chamber, and measurement of the grey level performed with Prism software. Note that aspirin effect is observed on dimethylsulfoxide (DMSO)-treated blood and $P2Y_{12}$ antagonism+epinephrine-treated blood.

A perfusion chamber assay on type III collagen (DMSO (vehicle) treated (a), full $P2Y_{12}$ antagonism (b), full $P2Y_{12}$ antagonism with epinephrine 20 μM(c)) have been performed before and 3 days after a daily dose of aspirin (325 mg). Results of the 2 blood donors are presented in FIG. 9. The data in FIG. 9 demonstrate that aspirin efficacy can be evaluated in absence or presence of $P2Y_{12}$ antagonism.

Example 4

An Arachidonic Acid-/Shear-Induced Platelet Aggregation Assay in Whole Blood

Platelets are labeled in whole blood with Rhodamine 6G as described above. Following addition of AA, blood will be perfused through 2 successive chambers which generate high (1500/sec) and low (50/sec) shear rates. The high shear rate induces platelet activation and aggregation is created by a sudden decrease in capillary diameter. The low shear rate area allows for the real time evaluation/quantification of the size of the platelet/platelet, platelet/leukocyte aggregates that will pass and/or adhere via the Simple PCI software or similar software capable of evaluating the size of the flowing thrombi.

In this example, a concentration of AA is used which will lead to thrombus formation in whole blood without occluding the proximal part of the channel. In other examples, the shear rates for both the proximal and distal parts of the channel are idealized.

Large mixed platelet/leukocyte aggregates are detectable in the low shear area (observable after less than 30 seconds) when whole blood is treated with 0.8 mM arachidonic acid and perfusion through a small uncoated circular capillary at 1700/sec followed by a larger capillary at 80/sec. These aggregates are not present in the absence of AA, and are prevented by the use of aspirin and a mixed TP/thromboxane synthase inhibitor (Terbogrel).

Once the profiles of the platelet/leukocyte aggregates are established, the effects of aspirin are evaluated. For example, an aspirin dose response study can be performed (by addition of liquid aspirin, ASPEGIC). Similarly, other antithrombotic agents (direct thrombin inhibitors (ANGIOMAX), $P2Y_{12}$ antagonists (5-chloro-N-[({4-[7-fluoro-6-(methylamino)-1-oxoisoquinolin-2(1H)-yl]phen- yl}amino)carbonyl]thiophene-2-sulfonamide) can be evaluated. A schematic representation of the chamber (Aspirin-Chip) is shown in FIG. 10.

Example 5

TP and PGD2 Antagonism Induces Dethrombosis

Figures 11A, 11B:
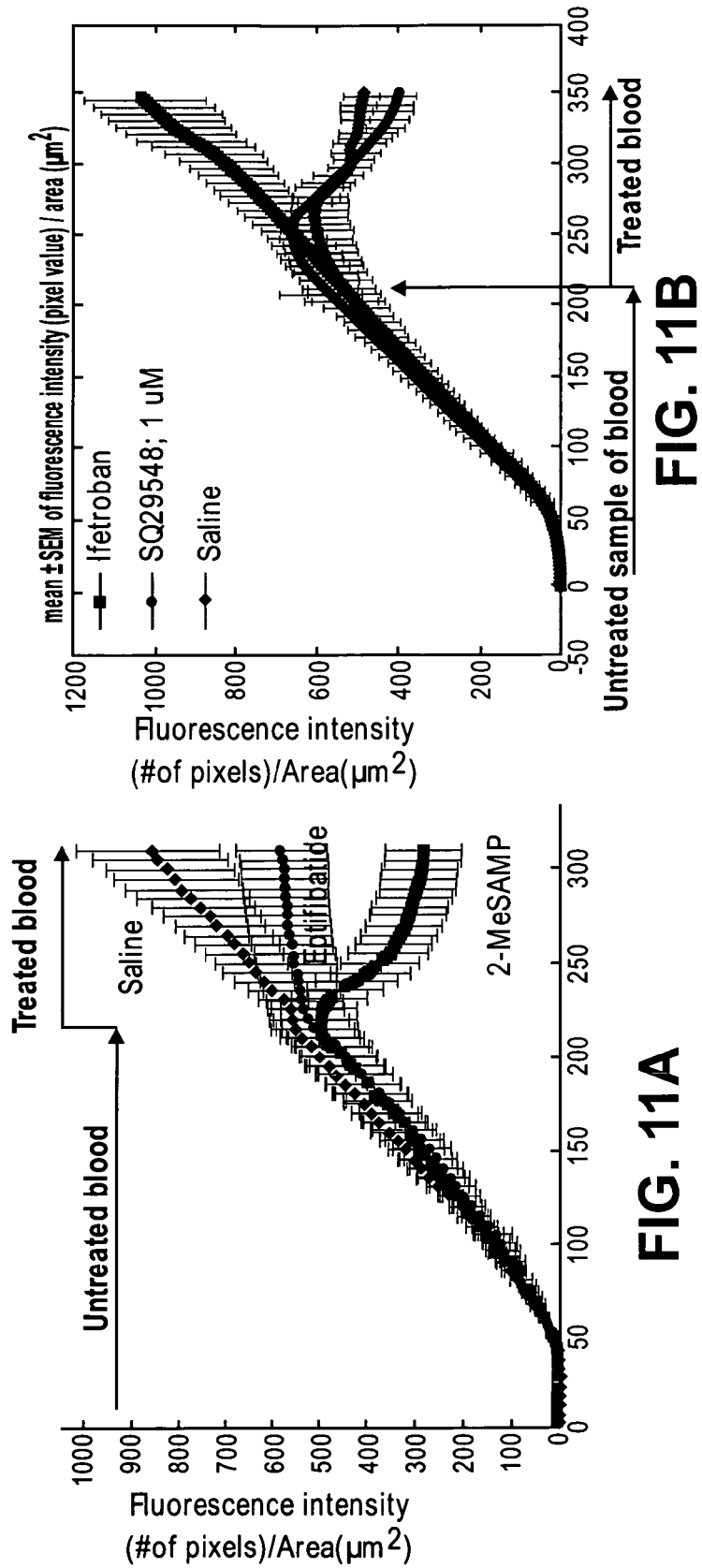
FIG. 11 shows how TP antagonism induces dethrombosis.
Figure 13:
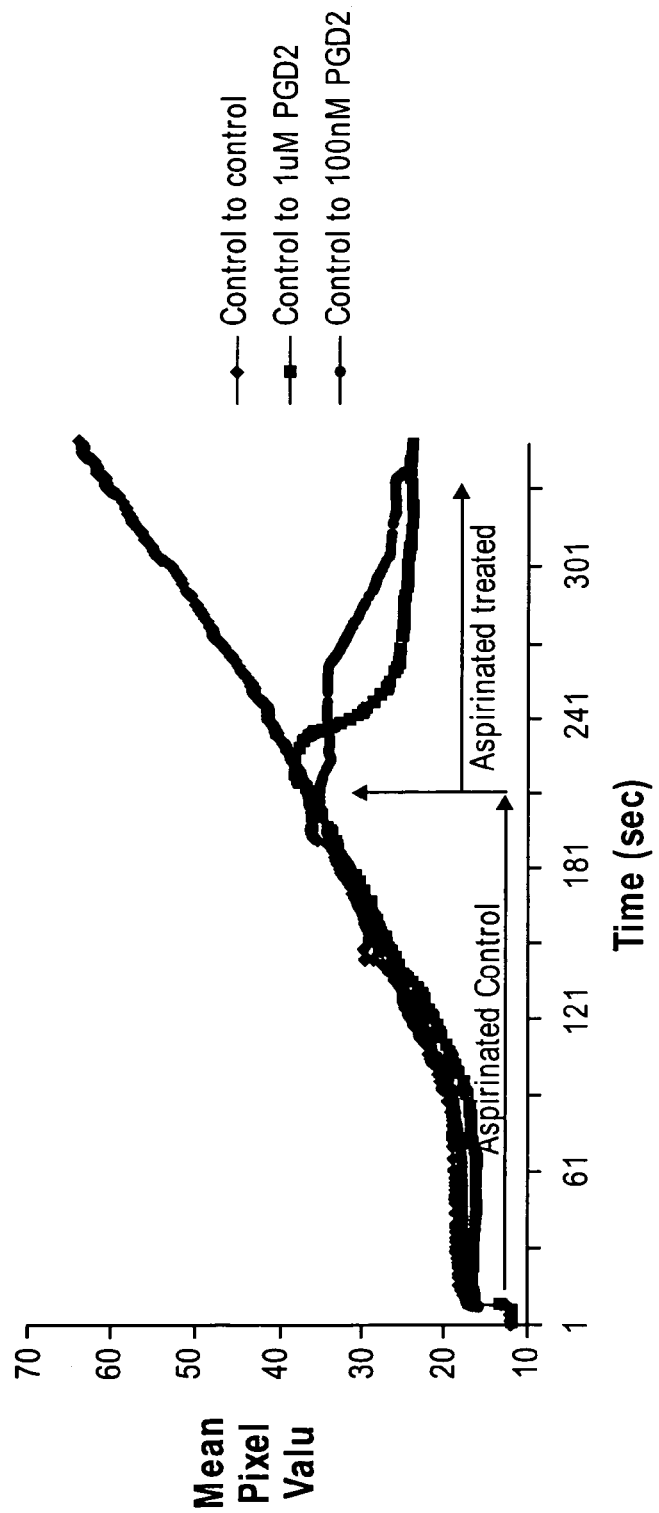
FIG. 13 shows how PGD2 induces dethrombosis on aspirin background.

Evaluation of the ability of thromboxane receptor (TP) antagonists to destabilize preformed thrombi was performed as followed in the real time thrombosis perfusion chamber assay (monitoring of fluorescently labeled platelets onto collagen coated surface). Untreated samples of blood were first perfused through the collagen-coated perfusion chamber for 210 seconds at 1500/sec. A second perfusion of blood treated with either (FIG. 11A); saline or 2.4 μM eptifibatide (therapeutic dose), 2-MeSAMP (a direct $P2Y_{12}$ antagonist at 100 μM a dose that totally blocks aggregation induced by ADP); or direct TP antagonists (FIG. 11B); SQ29548 (1 μM) and Ifetroban; 0.3 μM) immediately followed the first perfusion. Thrombus growth was stopped by the addition of eptifibatide with no apparent destabilization (FIG. 11A; mean slope after first perfusion (mSAFP): saline, 2.7±0.3 n=7; eptifibatide, 0.17±0.22, n=7, p<0.05 vs saline). Addition of 100 μM 2-MeSAMP caused sudden destabilization of preformed thrombi resulting in marked dethrombosis (FIG. 11A; mSAFP=−1.8±0.2, n=7, p<0.001 vs eptifibatide and p<0.0001 vs saline). TP antagonism lead to a strong destabilization of preformed thrombi (FIG. 1B; Ifetroban; mSAFP=−2.5±0.6; n=6, p<0.0001 vs saline). Aspirin alone (saline control) induced a slow and moderate destabilization of the thrombi (FIG. 12A; mSAFP=−1.07±0.3). Addition of 2MeSAMP and eptifibatide to aspirinated blood immediately arrested thrombus growth and induced sudden dethrombosis (p<0.05 vs respective monotherapies and aspirin alone). FIG. 12A; 2-MeSAMP 100 μM, mSAFP=−4.1±0.7; n=7; eptifibatide (mSAFP=−2.6±0.9; n=7). The presence of aspirin abolished the destabilization effects of Ifetroban (FIG. 12B). Since Cox-1 inhibition is known to prevent the synthesis of second messengers that are pro-aggregatory (TxA2) but also anti-aggregatory (i.e. PGD2), whereas TP antagonism only affects the binding of TxA2 to TP, endogenous inhibitory messenger like PGD2 in untreated samples of blood but not in aspirin-treated blood may account for the stronger destabilization activity of inhibitors of the TP receptor. In order to evaluate a possible role for PGD2 in mediating thrombus destabilization, aspirinated blood was perfused in presence of PDG2 over preformed aspirinated thrombi. This resulted in a significant, spontaneous reversal of thrombosis (FIG. 13; profiles of platelet deposition (mean pixel value) in collagen-coated perfusion chamber. Representative of 3 independent experiments).

This indicates that signaling pathways leading to increased cAMP levels (via inhibition of P2Y$_{12}$ or agonist activity of PDG2) confers thrombus instability, and that TP antagonists could be used for treatment of AMI in combination with P2Y$_{12}$ antagonists but not in combination with aspirin. Thus in one embodiment, thromboxane A2 receptor antagonist induces dethrombosis. In another embodiment, thrombosis can be inhibited by increasing cAMP levels via P2Y$_{12}$ antagonism or via PGD2 stimulation.

All publications, patents, accession number, patent applications and references cited in this specification are herein incorporated by reference in their entirety for all purposes as if each individual publication or patent application were specifically and individually indicated to be incorporated by reference.

While the present invention has been disclosed with reference to certain embodiments, numerous modifications, alterations and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method of evaluating aspirin responsiveness in a subject, comprising:
   (a) perfusing a blood sample from a subject through a channel in a perfusion device, wherein the channel has a coating which produces a blood deposit when exposed to blood and wherein the perfusion device comprises a pump which draws the blood through the channel at a selected shear rate, producing a blood deposit; wherein the perfusion device provides real time measurements of (1) the thrombotic profile of aspirin effects in addition to P2Y$_{12}$ antagonism in a collagen-coated perfusion chamber assay under arterial shear rates and (2) arachidonic acid/shear-induced platelet aggregation assay in whole blood under high shear rates; and
   (b) determining a status of aspirin responsiveness by measuring the level of blood deposited in the chamber and comparing the measured level of deposited blood with a control level of deposited blood, wherein said control level is selected from the group consisting of (1) a level measured using a sample of blood from said subject which has been treated with aspirin; (2) a level measured using a sample of blood from said subject which has been contacted with a thromboxane A2 receptor antagonist; and (3) a level previously determined to correspond to a status of aspirin responsiveness.

2. The method of claim 1, wherein whole unfractionated blood is pumped through the perfusion device.

3. The method of claim 1, wherein the blood sample is not treated with an anticoagulant.

4. The method of claim 1, wherein the blood sample is treated with an anticoagulant.

5. The method of claim 4, wherein the anticoagulant is selected from the group consisting of citrate, phenylalanine-proline-arginine-chloromethylketone and heparin.

6. The method of claim 1, wherein said selected shear rate is an arterial shear rate.

7. The method of claim 1, wherein said perfusion device further comprises a substantially flat transparent housing, wherein said channel extends through the housing with an inlet end for receiving a continuous flow of blood and an outlet end for discharging the blood.

8. The method of claim 1, wherein said coating comprises a coating selected from a group consisting of fibrillar collagen type III, fibrillar collagen type I, fibrinogen and tissue factor.

9. The method of claim 1, wherein the rate of blood deposit is sufficient to determine the extent of aspirin responsiveness within approximately 5 minutes of the start of perfusion.

10. The method of claim 1, wherein the measurement of the rate of blood deposit comprises
    obtaining images of the deposited blood, and
    calculating the levels of deposited blood from the images, wherein said images are obtained at least once every ten seconds during perfusion.

11. The method of claim 1, wherein said coating is human type III collagen and wherein said subject has been administered aspirin, further comprising the addition of an ADP-receptor antagonist to the sample, wherein said concentration of said antagonist in the sample is sufficient to cause a 50% inhibition of platelet aggregation relative to a sample which has been treated with aspirin but not treated with said ADP-receptor antagonist.

12. The method of claim 11, wherein said concentration of platelet ADP-receptor antagonist is approximately 10 μM.

13. The method of claim 1, wherein said method is insensitive to the presence of therapeutic amounts of platelet ADP-receptor antagonists in the subject's bloodstream.

14. The method of claim 1, wherein the subject has previously been administered a compound selected from the group consisting of a GP IIb-IIIa inhibitor, dipyridamole, PLAVIX (clopidogrel bisulfate), (ticlopidine HCl), or a non-steroidal anti-inflammatory drug.

* * * * *